United States Patent
Nikitenko et al.

(10) Patent No.: US 10,040,896 B2
(45) Date of Patent: Aug. 7, 2018

(54) SILANE FUNCTIONALIZED COMPOUNDS AND COMPOSITIONS THEREOF

(71) Applicant: Hexion Inc., Columbus, OH (US)

(72) Inventors: Antonina Nikitenko, Tarrytown, NY (US); Matthew Pinnow, Millwood, NY (US); Amitabh Bansal, Sugar Land, TX (US)

(73) Assignees: HEXION, INC., Columbus, OH (US); MOMENTIVE PERFORMANCE MATERIALS INC., Waterford, NY (US)

(*) Notice: Subject to any disclaimer, the term of this patent is extended or adjusted under 35 U.S.C. 154(b) by 0 days.

(21) Appl. No.: 14/863,054

(22) Filed: Sep. 23, 2015

(65) Prior Publication Data

US 2016/0090439 A1 Mar. 31, 2016

Related U.S. Application Data

(60) Provisional application No. 62/055,313, filed on Sep. 25, 2014.

(51) Int. Cl.
| | |
|---|---|
| *C08G 59/14* | (2006.01) |
| *C08L 63/00* | (2006.01) |
| *C09D 163/00* | (2006.01) |
| *C08G 18/58* | (2006.01) |
| *C07F 7/18* | (2006.01) |

(52) U.S. Cl.
CPC ........ *C08G 59/1438* (2013.01); *C07F 7/1836* (2013.01); *C08G 18/58* (2013.01); *C08G 18/588* (2013.01); *C08G 59/1477* (2013.01); *C08L 63/00* (2013.01); *C09D 163/00* (2013.01)

(58) Field of Classification Search
CPC ...................... C07F 7/18; C07F 7/1804; C07F 7/1812–7/1844; C08G 18/58; C08G 18/588; C08G 2261/144; C08G 59/1477; C08G 59/1438; C08L 63/00–63/10; C09D 163/00–163/10
See application file for complete search history.

(56) References Cited

U.S. PATENT DOCUMENTS

| | | |
|---|---|---|
| 3,327,016 A | 6/1967 | Lee et al. |
| 5,019,607 A * | 5/1991 | Coltrain ................ C08G 18/58 523/435 |
| 6,071,990 A | 6/2000 | Yip et al. |
| 7,803,958 B2 | 9/2010 | Gonzalez et al. |
| 9,404,014 B2 | 8/2016 | Heine et al. |
| 2008/0269376 A1 | 10/2008 | Ingrisch et al. |
| 2010/0216951 A1 | 8/2010 | Webster et al. |
| 2015/0353741 A1 | 12/2015 | Liao |
| 2015/0361211 A1 * | 12/2015 | Chun .................... C07F 7/1836 428/76 |

FOREIGN PATENT DOCUMENTS

| | | | |
|---|---|---|---|
| JP | H01116099 | 5/1989 | |
| WO | WO 2014129877 A1 * | 8/2014 | ............ C07F 7/1836 |

* cited by examiner

*Primary Examiner* — Kregg T Brooks

(57) ABSTRACT

Compositions comprising Silane functionalized compounds are provided. In one embodiment, the silane functionalized compounds include an epoxy resin derived backbone having silane functional groups pendant to the backbone or serving as end caps. The compositions comprising silane functionalized compounds may be utilized in a variety of applications including in coating formulations, adhesive formulations, composite materials, and combinations thereof.

20 Claims, 4 Drawing Sheets

SILANE FUNCTIONALIZED COMPOUNDS AND COMPOSITIONS THEREOF

RELATED APPLICATION DATA

This application claims benefit to U.S. Provisional Application No. 62/055,313 filed Sep. 25, 2014 of which the entire contents of the application are incorporated by reference herein.

FIELD OF THE INVENTION

The present invention relates to silane functionalized compounds which include a silane functionalized compound derived from an epoxy resin backbone. The silane functionalized compounds include an epoxy resin derived backbone having silane groups pendant to the backbone or serving as end caps. The present invention also relates to compositions comprising the silane functionalized compounds which may be utilized in a variety of applications.

BACKGROUND

Many high performance coatings, adhesives and sealants known in the art include resin systems based on epoxies, epoxy-siloxanes, acrylate siloxanes, polyurethanes, polyols, acrylates and polyesters. These systems are generally supplied as two separate components (2K), with one component being a resin and the other a curing agent, which components are mixed just before application.

These resin systems are employed in a variety of applications including coatings, adhesives, laminates and composites. 2K resin systems are utilized in a wide variety of functional and decorative applications including corrosion resistant coatings for underground pipe and steel reinforcing bars, electrical insulating coatings, appliance coatings, and finishes for automotive parts. These coatings offer good adhesion, hardness and impact resistance as well as protection from a variety of chemical and corrosive environments. However, these coatings may show loss of performance when exposed to UV radiation, weathering, or utilized under hot, wet conditions.

There is a need to provide resin compositions that exhibit suitable properties including, but not limited to, flexibility, impact resistance, easily cleaned, superior adhesion, weather resistance, and combinations thereof.

In addition, 2K system must be used soon after mixing with any unused portion discarded, resulting in inefficient processing and usage. There is also a need in the art to provide single component (1K) resin compositions that may be used without the need to mix beforehand, that have exceptional chemical resistance and durability.

SUMMARY

The present invention provides silane functionalized compounds which compounds include a silane functionalized compound derived from an epoxy resin backbone, which may also be referred to herein as a "silane functionalized derivative". The present invention also provides compositions comprising such silane functionalized compounds. The compounds and compositions are suitable for use in a variety of applications including, but not limited to, use in coatings, primers, adhesives, electronic materials, composites, and combinations thereof.

In one aspect, the present invention provides a silane functionalized epoxy resin derivative comprising an epoxy backbone with the glycidyl ether units of the epoxy opened with a nucleophile and silane groups pendant to the formed backbone. In one embodiment, the pendant group comprising the silane functional group is attached to the epoxy backbone through a linkage to pendant hydroxyl groups derived from the opening of the glycidyl ether units of the epoxy.

In one embodiment, the nucleophile comprises an amine.

In one embodiment, the pendant group comprises an alkoxy silane. In one embodiment, the pendant group comprises an (alkoxysilane)alkyl carbamate and is introduced via reaction of (alkoxysilane)alkyl isocyanate with pendant hydroxyl groups derived from the opening of the glycidyl ether units of the epoxy.

In one embodiment, the pendant group comprising the silane functional group is attached to a nucleophile used for the opening of the glycidyl ether units.

In one embodiment, the nucleophile comprises an alkoxysilane functionalized amine.

In one aspect, the present invention provides a silane functionalized epoxy resin compound that contains both epoxy groups and silane groups pendant to the epoxy backbone. The epoxy backbone is formed via a chain extension reaction that involves a bivalent linker molecule. The linker connects two or more epoxy molecules through opening of the glycidyl ether units. In one embodiment, the pendant group comprising the silane functional group is attached to the epoxy backbone through a linkage to pendant hydroxyl groups along the epoxy backbone derived from the opening of the glycidyl ether units of the epoxy.

In one aspect, the chain-extended epoxy resin compound undergoes opening of the end glycidyl ether units with a nucleophile and forms the chain-extended epoxy resin derivative. In one embodiment, the pendant group comprising the silane functional group is attached to the epoxy backbone through a linkage to pendant hydroxyl groups derived from the opening of the glycidyl ether.

In one embodiment, the silane functionalized epoxy resin and epoxy resin derivative is substantially free of any residual hydroxyl groups.

In one embodiment, the silane functionalized epoxy resin compound and epoxy resin derivative contain both (alkoxysilane)alkyl carbamate and non-silylated carbamate pendant groups.

In one embodiment, the alkoxysilane and alkyl components of the (alkoxysilane)alkyl carbamate independently comprise 1 to 10 carbon atoms.

In one embodiment, the compound has a weight average molecular weight of from about 350 to about 500,000.

In another aspect, the present invention provides a method of forming a silane functionalized compound comprising: (a) chain extending an epoxy resin with a suitable bifunctional reactant to provide a chain extended epoxy resin comprising secondary hydroxyl groups pendant to the epoxy resin backbone; and (b) grafting a silane containing compound to the pendant hydroxyl groups of the epoxy backbone.

In one embodiment, the method comprises end capping the silane functionalized compound with a secondary amine comprising an alkoxysilane.

In one embodiment a composition is provided including a silane functionalized compound having the formula:

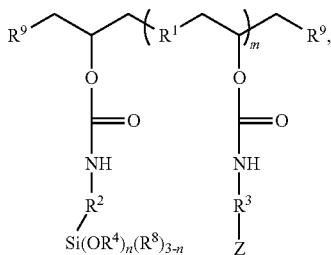

wherein
R$^1$=

Wherein m is greater than or equal to 1, x is from 0 to 20, y is from 0 to 20, R$^2$ and R$^3$ independently comprise an alkyl group, cycloalkyl group, or an aryl group with 1 to 30 carbon atoms, R$^4$ is an alkyl group with 1 to 8 carbon atoms, R$^8$ is an alkyl group with 1 to 10 carbon atoms, R$^9$ comprises a nucleophile unit selected from an amino group, a hydroxyl group, a carboxy group, or a thiol group, R$^{10}$ is a cyclical component from 3 to 30 carbon atoms, R$^{11}$ comprises an aliphatic component from 1 to 30 carbon atoms, Z comprises a hydrogen atom or Si(OR$^4$)$_n$(R$^8$)$_{3-n}$ group with n comprising 0.1 to 3, and optionally, a catalyst, a curing agent, or both.

In one embodiment a composition is provided including a silane functionalized compound having the formula:

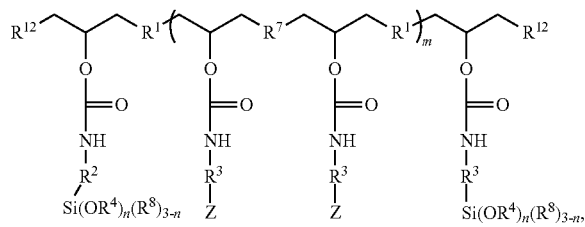

wherein
R$^1$=

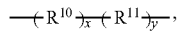

wherein m is greater than or equal to 1, x is from 0 to 20, y is from 0 to 20, R$^2$ and R$^3$ independently comprise an alkyl group, cycloalkyl group, or an aryl group with 1 to 30 carbon atoms, R$^4$ is an alkyl group with 1 to 8 carbon atoms, R$^8$ is an alkyl group with 1 to 10 carbon atoms, R$^7$ comprises a bisphenol, a bis-thiol, a dicarboxylic acid, a bis-secondary amine, or a primary amine, R$^{10}$ is a cyclical component from 3 to 30 carbon atoms, R$^{11}$ comprises an aliphatic component from 1 to 30 carbon atoms, R$^{12}$ comprises formula N(R$^5$D)$_a$(R$^6$D)$_b$, which R$^5$ and R$^6$ may each independently be phenyl, methyl ethanolamine reacted with an isocyanate silane, or have the formula (—CHR$^{13}$—)$_f$ with f from 1 to 20, and R$^{13}$ is hydrogen or a hydrocarbon group from 1 to 10 carbon atoms, D is either a hydrogen atom or —O(CO)NH—R$^3$—Z group, and a is from 0 to 2 and b is from 0 to 2, where one of a or b is a non-zero number, Z comprises a hydrogen atom or Si(OR$^4$)$_n$(R$^8$)$_{3-n}$ group with n comprising 0.1 to 3; and optionally, a catalyst, a curing agent, or both.

DETAILED DESCRIPTION OF THE FIGURES

The following is a brief description of figures wherein like numbering indicates like elements.

DETAILED DESCRIPTION

Figure 1:
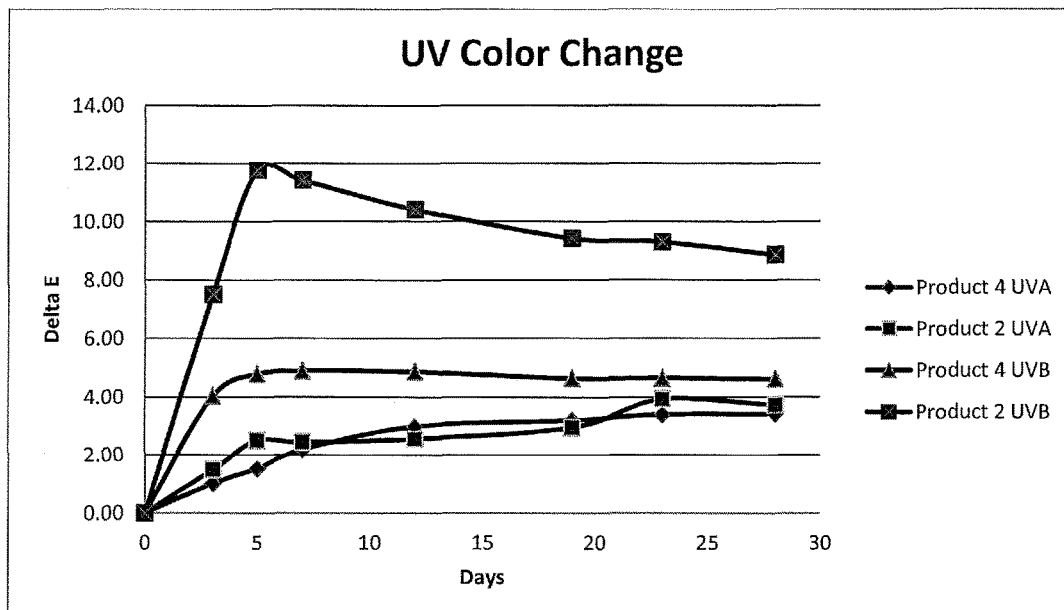
FIG. 1 is a chart illustrating the change in UV color over time.

The present invention provides silane functionalized compounds which compounds include a silane functionalized compound derived from an epoxy resin, which may also be referred to herein as a "silane functionalized derivative". The present invention also provides compositions comprising such silane functionalized compounds.

Silane Functionalized Compounds

The silane functionalized compounds of the invention include an epoxy resin derived backbone, with at least one silane group pendant to the backbone. The silane may be attached to the backbone through a linkage to a pendant reactive hydroxyl group.

The pendant hydroxyl group may be formed from the opening of the backbone's glycidyl ether units. Pendant hydroxyl groups may also be formed by the opening of the glycidyl ether units during the process of chain extension of the epoxy resin. The pendant hydroxyl group may be formed from the opening of the backbone's glycidyl ether units by a non-hydroxyl containing nucleophile, for example diethylamine. Additional pendant hydroxyl groups may be formed by the opening of the backbone's glycidyl ether units by a hydroxyl containing nucleophile, for example diethanolamine. Further pendant hydroxyl groups may be formed by the opening of the glycidyl ether units during the process of chain extension of the epoxy resin or through the hydroxyl group of the nucleophile, which for example may be a hydroxyl containing amine.

The epoxy resins useful in preparing the silane functionalized compounds of the invention may be saturated or unsaturated, aliphatic, cycloaliphatic, aromatic or heterocyclic and may contain pendant hetero-atoms and functional groups. The epoxy resin may also be monomeric or polymeric. The epoxy resin compound utilized may be, for example, an epoxy resin or a combination of epoxy resins prepared from an epihalohydrin and a phenol or a phenol type compound, prepared from an epihalohydrin and an amine, prepared from an epihalohydrin and a carboxylic acid, prepared from an epihalohydrin and compounds having at least one aliphatic or cycloaliphatic hydroxyl group, or prepared from the oxidation of unsaturated compounds.

In one embodiment, the epoxy resin includes those resins produced from an epihalohydrin and a phenol or a phenol type compound. The phenol type compound includes compounds having an average of more than one aromatic hydroxyl group per molecule. Examples of phenol type compounds include dihydroxy phenols, biphenols, bisphenols, halogenated biphenols, halogenated bisphenols, hydrogenated bisphenols, alkylated biphenols, alkylated bisphenols, trisphenols, phenol-aldehyde resins, novolac resins (i.e. the reaction product of phenols and simple aldehydes, preferably formaldehyde), halogenated phenol-aldehyde novolac resins, substituted phenol-aldehyde novolac resins, phenol-hydrocarbon resins, substituted phenol-hydrocarbon resins, phenol-hydroxybenzaldehyde resins, alkylated phenol-hydroxybenzaldehyde resins, hydrocarbon-phenol resins, hydrocarbon-halogenated phenol resins, hydrocarbon-alkylated phenol resins, or combinations of two or more thereof.

In another embodiment, the epoxy resin includes those resins produced from an epihalohydrin and bisphenols, halogenated bisphenols, hydrogenated bisphenols, novolac resins, and polyalkylene glycols, or combinations of two or more thereof.

In another embodiment, the epoxy resin includes those resins produced from an epihalohydrin and resorcinol, catechol, hydroquinone, biphenol, bisphenol A, bisphenol AP (1,1-bis(4-hydroxyphenyl)-1-phenyl ethane), bisphenol F, bisphenol K, tetrabromobisphenol A, phenol-formaldehyde novolac resins, alkyl substituted phenol-formaldehyde resins, phenol-hydroxybenzaldehyde resins, cresol-hydroxybenzaldehyde resins, dicyclopentadiene-phenol resins, dicyclopentadiene-substituted phenol resins, tetramethylbiphenol, tetramethyl-tetrabromobiphenol, tetramethyltribromobiphenol, tetrachlorobisphenol A, hydrogenated bisphenol A, 1,4-cyclohexanediol, 1,4-cyclohexane dimethanol, or combinations thereof.

The preparation of epoxy resins is known in the art. See Kirk-Othmer, Encyclopedia of Chemical Technology, 3rd Ed., Vol. 9, pp 267-289. Examples of epoxy resins and their precursors suitable for use in the compositions of the invention are also described, for example, in U.S. Pat. Nos. 5,137,990 and 6,451,898 which are incorporated herein by reference.

Examples of suitable epoxy resin components include, but are not limited to, EPON™ Resins 825, 826, 828, 862 and 1001 commercially available from Hexion Inc., of Columbus, Ohio.

In another embodiment, the epoxy resin includes those resins produced from an epihalohydrin and an amine. Suitable amines include diaminodiphenylmethane, aminophenol, xylene diamine, anilines, and the like, or combinations of two or more thereof.

In another embodiment, the epoxy resin includes those resins produced from an epihalohydrin and a carboxylic acid. Suitable carboxylic acids include phthalic acid, isophthalic acid, terephthalic acid, tetrahydro- and/or hexahydrophthalic acid, endomethylenetetrahydrophthalic acid, isophthalic acid, methylhexahydrophthalic acid, and the like or combinations thereof.

In another embodiment, the epoxy resin includes those resins produced from an epihalohydrin and compounds having at least one aliphatic or cycloaliphatic hydroxyl group. In this embodiment, it is understood that such resin compositions contain an average of more than one hydroxyl groups. Examples of compounds having at least one aliphatic or cycloaliphatic hydroxyl group per molecule include aliphatic or cycloaliphatic alcohols, glycols, polyols, polyether diols, polyether triols, polyether tetrols, any combination thereof and the like. Examples of the glycols or polyols include, but are not limited to, 1,4-butanediol, 1,5-pentanediol, 1,6-hexanediol, neopentyl glycol, cyclohexanedimethanol, hydrogenated BPA, polyethylene glycol, polypropylene glycol, trimethylolethane, trimethylolpropane and mixtures thereof. Examples of polyglycidyl ethers of an aliphatic glycols include 1,6 hexanediol diglycidyl ether (HDDGE) and 1,4 butanediol diglycidyl ether (BDDGE). Commercially available examples include, but are not limited to, HELOXY Modifier 32 (a diglycidyl ether of a polypropylene oxide) glycol), HELOXY Modifier 68 (the diglycidyl ether of neopentyl glycol), HELOXY Modifier 67 (a diglycidyl ether of 1,4 butanediol), HELOXY HD (a diglycidyl ether of 1,6 hexanediol), and HELOXY Modifier 107 (the diglycidyl ether of 1,4-cyclohexanedimethanol) all available from Hexion Inc.

In another embodiment the epoxy resin refers to an advanced epoxy resin which is the reaction product of one or more epoxy resins components, as described above, with one or more phenol type compounds and/or one or more compounds having an average of more than one aliphatic hydroxyl group per molecule as described above. Alternatively, the epoxy resin may be reacted with a carboxyl substituted hydrocarbon, which is described herein as a compound having a hydrocarbon backbone, preferably a $C_1$-$C_{40}$ hydrocarbon backbone, and one or more carboxyl moieties, preferably more than one, and most preferably two. The $C_1$-$C_{40}$ hydrocarbon backbone may be a straight- or branched-chain alkane or alkene, optionally containing oxygen. Fatty acids and fatty acid dimers are among the useful carboxylic acid substituted hydrocarbons. Included in the fatty acids are caproic acid, caprylic acid, capric acid, octanoic acid, VERSATIC™ acids, available from Hexion Inc., Columbus, Ohio, decanoic acid, lauric acid, myristic acid, palmitic acid, stearic acid, palmitoleic acid, oleic acid, linoleic acid, linolenic acid, erucic acid, pentadecanoic acid, margaric acid, arachidic acid, and dimers thereof.

In another embodiment, the epoxy resin is the reaction product of a polyepoxide and a compound containing more than one isocyanate moiety or a polyisocyanate. Preferably the epoxy resin produced in such a reaction is an epoxy-terminated polyoxazolidone.

The epoxy resin derived backbone may be a chain extended epoxy. Chain extended epoxy resins and epoxy derived resins may be produced by reacting a bifunctional epoxy material with a bifunctional alcohol (a diol), carboxylic acid, isocyanate, phenol, amine, and combinations thereof. In one embodiment, the material to facilitate the chain extension is selected from a diol including, but not limited to, an aliphatic diol, a cycloaliphatic diol, a polyether diol, an aromatic diol, a bisphenol derivative aromatic diol, and combinations thereof. In one embodiment, the diol is bisphenol A. Aliphatic and aromatic dicarboxylic acids such as succinic acid, adipic acid, azelaic acid, dodecanedioic acid, dimer, phthalic acid, isophthalic acid, terephthalic acid, and combinations thereof, may also be used in the chain extending reaction.

The diol for the chain-extended backbone may be derived from a short-chain diepoxide. In one embodiment, the diol is a derivative of hydrogenated bisphenol A; the chain extension is facilitated with bis-isocyanate, taken in excess, and the resulting isocyanate-functioned chain-extended epoxy derivative is capped with (alkoxysilano)alkyl amine.

Before the epoxy compound is modified with silane, epoxide (diglycidyl ether groups) at the terminal ends of the compound may be end capped with another group as desired for a particular purpose or intended use. Suitable groups to end cap the compound include an amine, an aminosilane, an amino disilane, (for example bis-(gamma-triethoxysilylpropyl) amine) and combinations thereof. The amino silanes and amino disilanes may include alkoxy silane functionalities.

The silane functional group is pendant to the epoxy resin derived backbone and may be selected as desired for a particular purpose or intended use. The silane functionality may comprise one or more alkoxy units (C—O—) to form an alkoxy silane. Examples of alkoxy silanes include trimethoxy silane, triethoxy silane, tripropoxysilane, and combinations thereof. The silane functional group may be linked to the epoxy derived backbone through a linking group or moiety that is reactive with a pendant hydroxyl group of the epoxy derived backbone. In one embodiment, the silane functionalized epoxy resins or the silane functionalized derivatives are provided by reacting an isocyanato silane with the epoxy resin or the epoxy derived resin. An example of a suitable isocyanato silane is a 3-(alkzoxysilane) alkyl isocyanate where the alkoxysilane and alkyl groups may contain 1 to 10 carbon atoms. A particularly suitable isocyanato silane includes, but is not limited to, 3-(triethoxysilane) propyl isocyanate.

The silane functionalized compounds on the invention may comprise zero, one, or more pendant hydroxyl functional groups in the final functionalized compound. In one embodiment, the silane functionalized compound is free of any pendant hydroxyl groups along the epoxy resin derived backbone, such as, substantially all the pendant hydroxyl groups have been functionalized with a pendant group comprising either a silane group or a non-silylated isocyanate derivative.

In one embodiment, the silane functionalized compound may be represented by Formula 1:

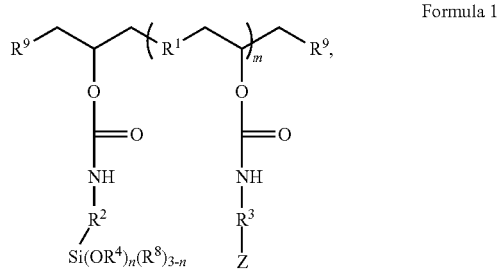

Formula 1 where
$R^1 =$

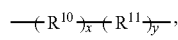

In Formula 1, $R^1$ may have x from 0 to 20, such as from 0.5 to 10, and from 1 to 2.5, where a non-zero x results in a $R^{10}$ cyclical component, that may be a homocyclic or heterocyclic saturated, unsaturated, or aromatic group from 3 to 30 carbon atoms; $R^1$ may have a y of 0 to 20, such as from 0 to 10, and from 0 to 2, where a non-zero y results in an $R^{11}$ aliphatic component where $R^{11}$ comprises from 1 to 30 carbon atoms; or $R^1$ may have a both non-zero x and a non-zero y resulting in both a cyclical component and an aliphatic component; and $R^1$ has at least a non-zero x or a non-zero y. If both x and y are present, the molar ratio of y to x may be 0.01 to 50, such as from 0.1 to 20, for example 0.4 to 1. The m is greater than or equal to 1, or m is 1 to 10, or 1 to 5, or 1 to 3.

In Formula 1 $R^2$ and $R^3$ are independently selected from a linear or branched alkyl, cycloalkyl, or aryl group with 1 to 30 carbon atoms, such as from 2 to 10 carbon atoms, for example, 3 to 5 carbon atoms, for the alkyl group, with 3 to 30 carbon atoms, such as from 3 to 10 carbon atoms, for example, 3 to 6 carbon atoms, for the cycloalkyl group, and with 6 to 30 carbon atoms, such as from 6 to 10 carbon atoms, for the aryl group. $R^9$ is a nucleophile unit selected from an amino group, a hydroxyl group, a carboxy group, a thiol group.

Z is either a hydrogen atom or $Si(OR^4)_n(R^8)_{3-n}$ group, with $R^4$ is an alkyl group with 1 to 8 carbon atoms, such as from 1 to 5 carbon atoms, for example, 1 to 3 carbon atoms, a cycloalkyl group with 3 to 8 carbon atoms, or an aryl group with 6 to 8 carbon atoms, n is 0.1 to 3, such as 1 to 3, for example, 2 to 3, and $R^8$ is an alkyl group with 1 to 10 carbon atoms, such as from 2 to 5 carbon atoms, for example, 2 to 3 carbon atoms.

In one embodiment, $R^1$ is a saturated or unsaturated, aliphatic, cycloaliphatic, aromatic or heterocyclic group having 1 to 30 carbon atoms, such as from 4 to 20 carbon atoms, for example, 6 to 16 carbon atoms, for aliphatic and heterocyclic groups; having 3 to 30 carbon atoms, such as from 4 to 20 carbon atoms, for example, 6 to 16 carbon atoms, for cycloaliphatic groups; and having 6 to 30 carbon atoms, such as from 6 to 20 carbon atoms, for example, 6 to 16 carbon atoms, for aromatic group; and $R^1$ may contain pendant hetero-atoms. Alternatively, $R^1$ is linear or branched alkyl with 1 to 30 carbon atoms or a cycloaliphatic with 3 to 30 carbon atoms or aryl unit with 6 to 30 carbon atoms.

In one embodiment, $R^1$ may be selected from the group comprising resorcinol, catechol, hydroquinone, bisphenol, bisphenol A, hydrogenated bisphenol A, 1,4-cyclohexanediol, 1,4-cyclohexane dimethanol, bisphenol AP (1,1-bis(4-hydroxylphenyl)-1-phenyl ethane), bisphenol F, bisphenol K, bisphenol M, 4,4-oxydiphenol, 4,4'-dihydroxybenzophenone, 4,4'-dihydroxybiphenyl, and 4,4'-dihydroxy-α-methylstilbene, and combinations thereof. $R^1$ may be selected from the group comprising bisphenol A, hydrogenated bisphenol A, 1,4-cyclohexane dimethanol, bisphenol F, and combinations thereof. Most preferred, $R^1$ may be bisphenol A, hydrogenated bisphenol A, and combinations thereof.

In one embodiment, $R^2$ may have the formula $R^2=(—CHR^{13}—)_f$ with f from 1 to 20, such as from 1 to 10, for example, from 2-5, and $R^{13}$ is hydrogen or a hydrocarbon group from 1 to 10 carbon atoms, such as from 1 to 5 carbon atoms, for example, 1 carbon atom. Examples of suitable $R^2$ components include n-propyl, n-butyl, n-pentyl, and n-hexyl, and combinations thereof, of which n-propyl or butyl are the most preferred.

In one embodiment, $R^3$ may be a phenyl component or have the formula $R^3=(—CHR^{14}—)_f$ with f from 1 to 20, such as from 1 to 10, for example, from 2-5, and $R^{14}$ is hydrogen or a hydrocarbon group from 1 to 10 carbon atoms, such as from 1 to 5 carbon atoms, for example, 1 carbon atom. Examples of suitable $R^2$ components include ethyl, propyl, pentyl, hexyl, cyclohexyl, phenyl, isopropyl, and butyl, preferably, ethyl, propyl, pentyl, hexyl, phenyl, and butyl, of which ethyl and phenyl are the most preferred.

In one embodiment, $R^4$ may be ethylene glycol or have the formula $R^4=(—CHR^{15}—)_f$ with f from 1 to 20, such as from 1 to 10, for example, from 2-5, and $R^{14}$ is hydrogen or a hydrocarbon group from 1 to 10 carbon atoms, such as from 1 to 5 carbon atoms, for example, 1 carbon atom. Examples of suitable $R^4$ components include methyl, ethyl, propyl, i-propyl, butyl, and ethylene glycol, preferably, methyl, ethyl, i-propyl, and ethylene glycol, of which methyl and ethyl are the most preferred.

In one embodiment, $R^9$ is selected from diethylamine, (2-methylamino)ethanol, diethanolamine, morpholine, and an amine containing alkoxysilane moiety. The amine containing alkoxysilane moiety may comprise $HN$—$(C_3H_6Si(OR^2)_3)_2$ with $R^2$=$(-CHR^{13}-)_f$ with f from 1 to 20, such as from 1 to 10, for example, from 2-5, and $R^{13}$ is hydrogen or a hydrocarbon group from 1 to 10 carbon atoms, such as from 1 to 5 carbon atoms, for example, 1 carbon atom. Examples of the amine containing alkoxysilane moiety include bis(trimethoxysilylpropyl)amine, N-ethyl-amino isobutyl trimethoxy silane, and combinations thereof.

In one embodiment, where m=1 in Formula 1, the silane functionalized compound may be represented by Formula 2:

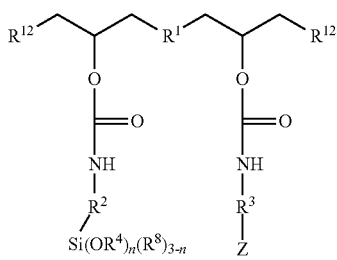

Formula 2 where
$R^1$=

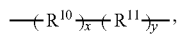

In Formula 2, $R^1$ may have x from 0 to 20, such as from 0.5 to 10, and from 1 to 2.5, where a non-zero x results in a $R^{10}$ cyclical component, that may be a homocyclic or heterocyclic saturated, unsaturated, or aromatic group from 3 to 30 carbon atoms; $R^1$ may have a y of 0 to 20, such as from 0 to 10, and from 0 to 2, where a non-zero y results in an $R^{11}$ aliphatic component where $R^{11}$ comprises from 1 to 30 carbon atoms; or $R^1$ may have a both non-zero x and a non-zero y resulting in both a cyclical component and an aliphatic component; and $R^1$ has at least a non-zero x or a non-zero y. If both x and y present, the molar ratio of y to x may be 0.01 to 50, such as from 0.1 to 20, for example 0.4 to 1.

In Formula 2, $R^2$ and $R^3$ are independently selected from a linear or branched alkyl, cycloalkyl, or aryl group with 1 to 30 carbon atoms, such as from 2 to 10 carbon atoms, for example, 3 to 5 carbon atoms, for the alkyl group, with 3 to 30 carbon atoms, such as from 3 to 10 carbon atoms, for example, 3 to 6 carbon atoms, for the cycloalkyl group, and with 6 to 30 carbon atoms, such as from 6 to 10 carbon atoms, for the aryl group.

$R^{12}$ is a derivative of $R^9$, and $R^{12}$ is represented by the formula $N(R^5D)_a(R^6D)_b$, which $R^5$ and $R^6$ may each independently be phenyl, methyl ethanolamine reacted with an isocyanate silane, or have the formula $R$=$(-CHR^{13}-)_f$ with f from 1 to 20, such as from 1 to 10, for example, from 2-5, and $R^{13}$ is hydrogen or a hydrocarbon group from 1 to 10 carbon atoms, such as from 1 to 5 carbon atoms, for example, 1 carbon atom, D is either a hydrogen atom or —O(CO)NH—$R^3$—Z group, and a is from 0 to 2, such as from 0.5 to 1.5, for example 0.9 to 1.1, b is from 0 to 2, such as from 0.5 to 1.5, for example 0.9 to 1.1, of which one of a or b is a non-zero number. Examples of suitable $R^5$ and $R^6$ components include diphenoxyamine, dialkylamine, dimethyl amine, diethylamine, dibutylamine, methyl ethanolamine reacted with an isocyanate silane, and combinations thereof, with dimethyl amine, diethylamine, dibutylamine, and methyl ethanolamine reacted with an isocyanate silane being the most preferred.

Z is either a hydrogen atom or $Si(OR^4)_n(R^8)_{3-n}$ group, with $R^4$ is an alkyl group with 1 to 8 carbon atoms, such as from 1 to 5 carbon atoms, for example, 1 to 3 carbon atoms, a cycloalkyl group with 3 to 8 carbon atoms, or an aryl group with 6 to 8 carbon atoms, n is 0.1 to 3, such as 1 to 3, for example, 2 to 3, and $R^8$ is an alkyl group with 1 to 10 carbon atoms, such as from 2 to 5 carbon atoms, for example, 2 to 3 carbon atoms.

In one embodiment, $R^1$ is a saturated or unsaturated, aliphatic, cycloaliphatic, aromatic or heterocyclic group having 1 to 30 carbon atoms, such as from 4 to 20 carbon atoms, for example, 6 to 16 carbon atoms, for aliphatic and heterocyclic groups; having 3 to 30 carbon atoms, such as from 4 to 20 carbon atoms, for example, 6 to 16 carbon atoms, for cycloaliphatic groups; and having 6 to 30 carbon atoms, such as from 6 to 20 carbon atoms, for example, 6 to 16 carbon atoms, for aromatic group; and $R^1$ may contain pendant hetero-atoms. Alternatively, $R^1$ is linear or branched alkyl with 1 to 30 carbon atoms or a cycloaliphatic with 3 to 30 carbon atoms or aryl unit with 6 to 30 carbon atoms.

In one embodiment, $R^1$ may be selected from the group comprising resorcinol, catechol, hydroquinone, bisphenol, bisphenol A, hydrogenated bisphenol A, 1,4-cyclohexanediol, 1,4-cyclohexane dimethanol, bisphenol AP (1,1-bis(4-hydroxylphenyl)-1-phenyl ethane), bisphenol F, bisphenol K, bisphenol M, 4,4-oxydiphenol, 4,4'-dihydroxybenzophenone, 4,4'-dihydroxybiphenyl, and 4,4'-dihydroxy-α-methylstilbene, and combinations thereof. $R^1$ may be selected from the group comprising bisphenol A, hydrogenated bisphenol A, 1,4-cyclohexane dimethanol, bisphenol F, and combinations thereof. Most preferred, $R^1$ may be bisphenol A, hydrogenated bisphenol A, and combinations thereof.

In one embodiment, $R^2$ may have the formula $R^2$=$(-CHR^{13}-)_f$ with f from 1 to 20, such as from 1 to 10, for example, from 2-5, and $R^{13}$ is hydrogen or a hydrocarbon group from 1 to 10 carbon atoms, such as from 1 to 5 carbon atoms, for example, 1 carbon atom. Examples of suitable $R^2$ components include n-propyl, n-butyl, n-pentyl, and n-hexyl, of which n-propyl or butyl are the most preferred.

In one embodiment, $R^3$ may be a phenyl component or have the formula $R^3$=$(-CHR^{14}-)_f$ with f from 1 to 20, such as from 1 to 10, for example, from 2-5, and $R^{14}$ is hydrogen or a hydrocarbon group from 1 to 10 carbon atoms, such as from 1 to 5 carbon atoms, for example, 1 carbon atom. Examples of suitable $R^2$ components include ethyl, propyl, pentyl, hexyl, cyclohexyl, phenyl, isopropyl, and butyl, preferably, ethyl, propyl, pentyl, hexyl, phenyl, and butyl, of which ethyl and phenyl are the most preferred.

In one embodiment, $R^4$ may be ethylene glycol or have the formula $R^4$=$(-CHR^{15}-)_f$ with f from 1 to 20, such as from 1 to 10, for example, from 2-5, and $R^{14}$ is hydrogen or a hydrocarbon group from 1 to 10 carbon atoms, such as from 1 to 5 carbon atoms, for example, 1 carbon atom.

Examples of suitable $R^4$ components include methyl, ethyl, propyl, i-propyl, butyl, and ethylene glycol, preferably, methyl, ethyl, i-propyl, and ethylene glycol, of which methyl and ethyl are the most preferred.

Alternatively, the silane functionalized compound may be represented by Formula 3:

Formula 3

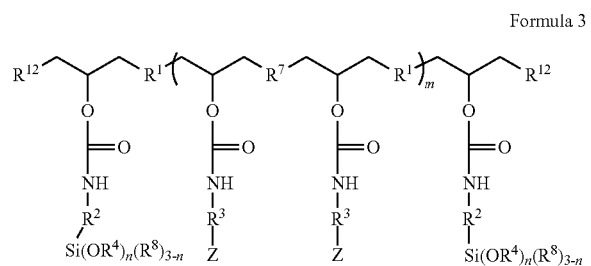

where
$R^1=$

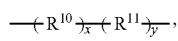

In Formula 3, $R^1$ may have x from 0 to 20, such as from 0.5 to 10, and from 1 to 2.5, where a non-zero x results in a cyclical component, that may be a homocyclic or heterocyclic saturated, unsaturated, or aromatic group from 3 to 30 carbon atoms; $R^1$ may have a y of 0 to 20, such as from 0 to 10, and from 0 to 2, where a non-zero y results in an R' aliphatic component where $R^{11}$ comprises from 1 to 30 carbon atoms; or $R^1$ may have a both non-zero x and a non-zero y resulting in both a cyclical component and an aliphatic component; and $R^1$ has at least a non-zero x or a non-zero y. If both x and y present, the molar ratio of y to x may be 0.01 to 50, such as from 0.1 to 20, for example 0.4 to 1. The m is greater than or equal to 1, or m is 1 to 10, or 1 to 5, or 1 to 3, and n is 0.1 to 3, such as 1 to 3, for example, 2 to 3.

In Formula 3, $R^2$ and $R^3$ are independently selected from a linear or branched alkyl, cycloalkyl, or aryl group with 1 to 30 carbon atoms, such as from 2 to 10 carbon atoms, for example, 3 to 5 carbon atoms, for the alkyl group, with 3 to 30 carbon atoms, such as from 3 to 10 carbon atoms, for example, 3 to 6 carbon atoms, for the cycloalkyl group, and with 6 to 30 carbon atoms, such as from 6 to 10 carbon atoms, for the aryl group.

$R^7$ is independently selected from a bis-thiol, a dicarboxylic acid, a bis-secondary amine, or a primary amine. The primary amine may have the formula $C_{18}H_{39}N$ or $C_{16}H_{35}N$. The secondary amine may be piperazine or symmetrical dimethyl ethylene diamine.

$R^{12}$ is a derivative of $R^9$, and $R^{12}$ may comprises an amine group represented by the formula $N(R^5C)_a(R^6C)_b$, which $R^5$ and $R^6$ may each independently be phenyl, methyl ethanolamine reacted with an isocyanate silane, or have the formula $R=(-CHR^{13}-)_f$ with f from 1 to 20, such as from 1 to 10, for example, from 2-5, and $R^{13}$ is hydrogen or a hydrocarbon group from 1 to 10 carbon atoms, such as from 1 to 5 carbon atoms, for example, 1 carbon atom, C is either a hydrogen atom or $-O(CO)NH-R^3-Z$ group, and a is from 0 to 2, such as from 0.5 to 1.5, for example 0.9 to 1.1, a is from 0 to 2, such as from 0.5 to 1.5, for example 0.9 to 1.1, of which one of a or b is a non-zero number. Examples of suitable $R^5$ and $R^6$ components include diphenoxyamine, dialkylamine, dimethyl amine, diethylamine, dibutylamine, methyl ethanolamine reacted with an isocyanate silane, an combinations thereof, with dimethyl amine, diethylamine, dibutylamine, and methyl ethanolamine reacted with an isocyanate silane being the most preferred.

Z is either a hydrogen atom or $Si(OR^4)_n(R^8)_{3-n}$ group, with $R^4$ is an alkyl group with 1 to 8 carbon atoms, such as from 1 to 5 carbon atoms, for example, 1 to 3 carbon atoms, a cycloalkyl group with 3 to 8 carbon atoms, or an aryl group with 6 to 8 carbon atoms, n is 0.1 to 3, such as 1 to 3, for example, 2 to 3, and $R^8$ is an alkyl group with 1 to 10 carbon atoms, such as from 2 to 5 carbon atoms, for example, 2 to 3 carbon atoms.

In one embodiment, $R^1$ is a saturated or unsaturated, aliphatic, cycloaliphatic, aromatic or heterocyclic group having 1 to 30 carbon atoms, such as from 4 to 20 carbon atoms, for example, 6 to 16 carbon atoms, for aliphatic and heterocyclic groups; having 3 to 30 carbon atoms, such as from 4 to 20 carbon atoms, for example, 6 to 16 carbon atoms, for cycloaliphatic groups; and having 6 to 30 carbon atoms, such as from 6 to 20 carbon atoms, for example, 6 to 16 carbon atoms, for aromatic group; and $R^1$ may contain pendant hetero-atoms. Alternatively, $R^1$ is linear or branched alkyl with 1 to 30 carbon atoms or a cycloaliphatic with 3 to 30 carbon atoms or aryl unit with 6 to 30 carbon atoms.

In one embodiment, $R^1$ may be selected from the group comprising resorcinol, catechol, hydroquinone, bisphenol, bisphenol A, hydrogenated bisphenol A, 1,4-cyclohexanediol, 1,4-cyclohexane dimethanol, bisphenol AP (1,1-bis(4-hydroxylphenyl)-1-phenyl ethane), bisphenol F, bisphenol K, bisphenol M, 4,4-oxydiphenol, 4,4'-dihydroxybenzophenone, 4,4'-dihydroxybiphenyl, and 4,4'-dihydroxy-α-methylstilbene, and combinations thereof. $R^1$ may be selected from the group comprising bisphenol A, hydrogenated bisphenol A, 1,4-cyclohexane dimethanol, bisphenol F, and combinations thereof. Most preferred, $R^1$ may be bisphenol A, hydrogenated bisphenol A, and combinations thereof.

In one embodiment, $R^2$ may have the formula $R^2=(-CHR^{13}-)_f$ with f from 1 to 20, such as from 1 to 10, for example, from 2-5, and $R^{13}$ is hydrogen or a hydrocarbon group from 1 to 10 carbon atoms, such as from 1 to 5 carbon atoms, for example, 1 carbon atom. Examples of suitable $R^2$ components include n-propyl, n-butyl, n-pentyl, and n-hexyl, of which n-propyl or butyl are the most preferred.

In one embodiment, $R^3$ may be a phenyl component or have the formula $R^3=(-CHR^{14}-)_f$ with f from 1 to 20, such as from 1 to 10, for example, from 2-5, and $R^{14}$ is hydrogen or a hydrocarbon group from 1 to 10 carbon atoms, such as from 1 to 5 carbon atoms, for example, 1 carbon atom. Examples of suitable $R^2$ components include ethyl, propyl, pentyl, hexyl, cyclohexyl, phenyl, isopropyl, and butyl, preferably, ethyl, propyl, pentyl, hexyl, phenyl, and butyl, of which ethyl and phenyl are the most preferred.

In one embodiment, $R^4$ may be ethylene glycol or have the formula $R^4=(-CHR^{15}-)_f$ with f from 1 to 20, such as from 1 to 10, for example, from 2-5, and $R^{14}$ is hydrogen or a hydrocarbon group from 1 to 10 carbon atoms, such as from 1 to 5 carbon atoms, for example, 1 carbon atom. Examples of suitable $R^4$ components include methyl, ethyl, propyl, i-propyl, butyl, and ethylene glycol, preferably, methyl, ethyl, i-propyl, and ethylene glycol, of which methyl and ethyl are the most preferred.

In one embodiment, $R^7$ is independently selected from a bis-thiol, a dicarboxylic acid, a bis-secondary amine, or a primary amine. The primary amine may have the formula $C_{18}H_{39}N$ or $C_{16}H_{35}N$. The secondary amine may be piperazine or symmetrical dimethyl ethylene diamine.

In one embodiment, where m is zero (0) in Formula 3, the silane functionalized compound may be represented by Formula 4:

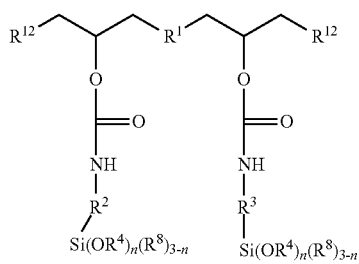

Formula 4 where
$R^1 =$

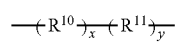

where the $R^1$, $R^2$, $R^3$, $R^4$, $R^8$, $R^{10}$, $R^{11}$, and $R^{12}$ values are defined as above for Formula 3. Formula 4 may also be derived from Formula 1, where in Formula 1 m is one (1), Z is a $Si(OR^4)_n(R^8)_{3-n}$ group, and $R^9$ is an amino group defined as $R^{12}$ herein.

In a further embodiment, the silane functionalized compound may be represented by Formula 5:

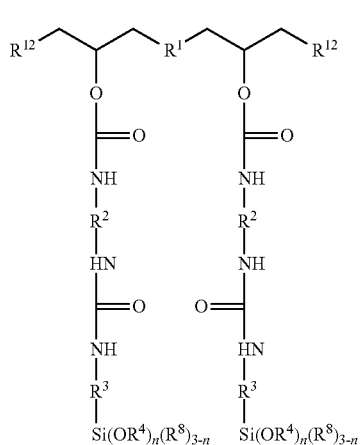

Formula 5

$R^1$, $R^2$, $R^3$, $R^4$, $R^8$, and $R^{12}$ values are defined as above for Formula 3.

In one embodiment, the silane functionalized compound may have a weight average molecular weight of from about 350 to about 500,000; from about 500 to about 100,000; from about 1,000 to about 50,000; even from about 1,000 to about 5,000. In one embodiment, the silane functionalized compound may have a weight average molecular weight of from about 350 to about 50,000. Here as elsewhere in the specification and claims, numerical values may be combined to form new and non-disclosed ranges.

In one embodiment, the silane functionalized compound is of the formula:

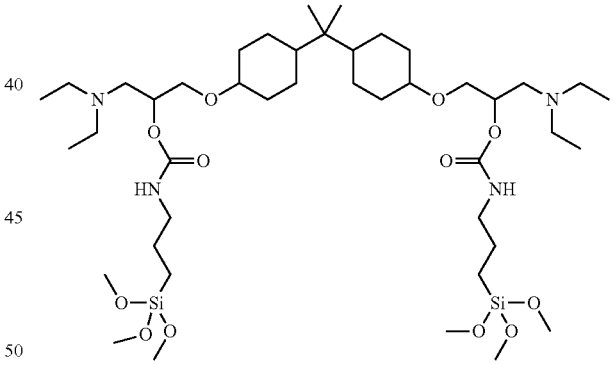

In one embodiment, silane functionalized compound is of the formula:

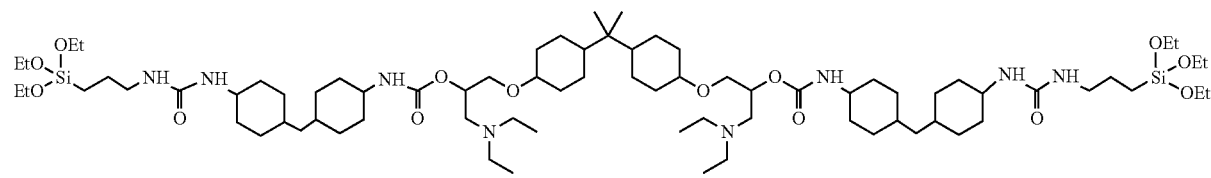 [SMILES: CCO[Si](CCCNC(=O)NC1CCC(CC2CCC(NC(=O)OC(COC3CCC(C(C)(C)C4CCC(OCC(CN(CC)CC)OC(=O)NC5CCC(CC6CCC(NC(=O)NCCC[Si](OCC)(OCC)OCC)CC6)CC5)CC4)CC3)CN(CC)CC)CC2)CC1)(OCC)OCC]

In one embodiment, the silane functionalized compound is of the formula:

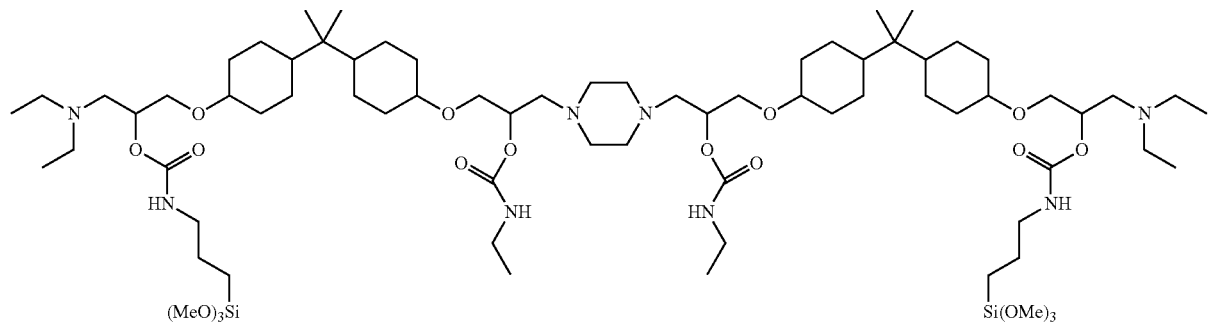

In one embodiment, the silane functionalized compound is of the formula:

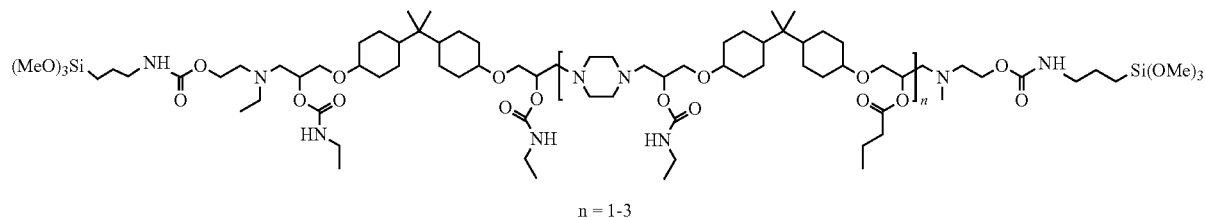

n = 1-3

In one embodiment, the silane functionalized compound may be formed by: (a) opening the glycidyl units of the epoxy with a secondary amine, and (b) reacting the hydroxyl groups, formed in the previous step, with (alkoxysilane) alkyl isocyanate, which may be used alone or mixed with non-silyl containing isocyanate, according to the following reaction Scheme 1:

The final product of Scheme 1 has the structure of Formula 2.

In one embodiment, the silane functionalized compound may be formed by: (a) opening the glycidyl units of the epoxy with a secondary amine, (b) chain-extending the intermediate with a bis-isocyanate, and (c) capping the terminal isocyanato groups with (alkoxysilyl) alkyl amine, according to the following reaction Scheme 2:

Scheme 1

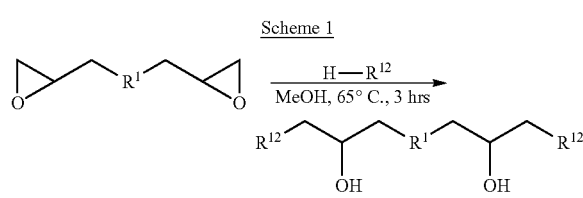

Scheme 2

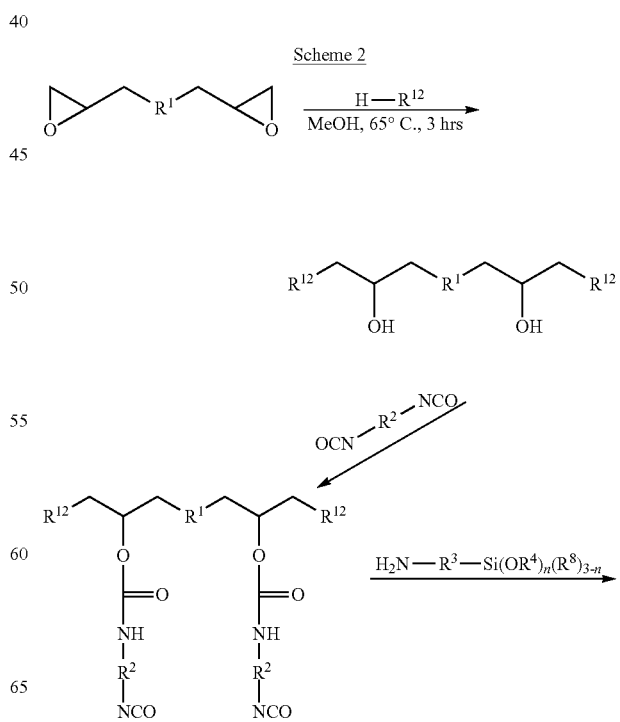

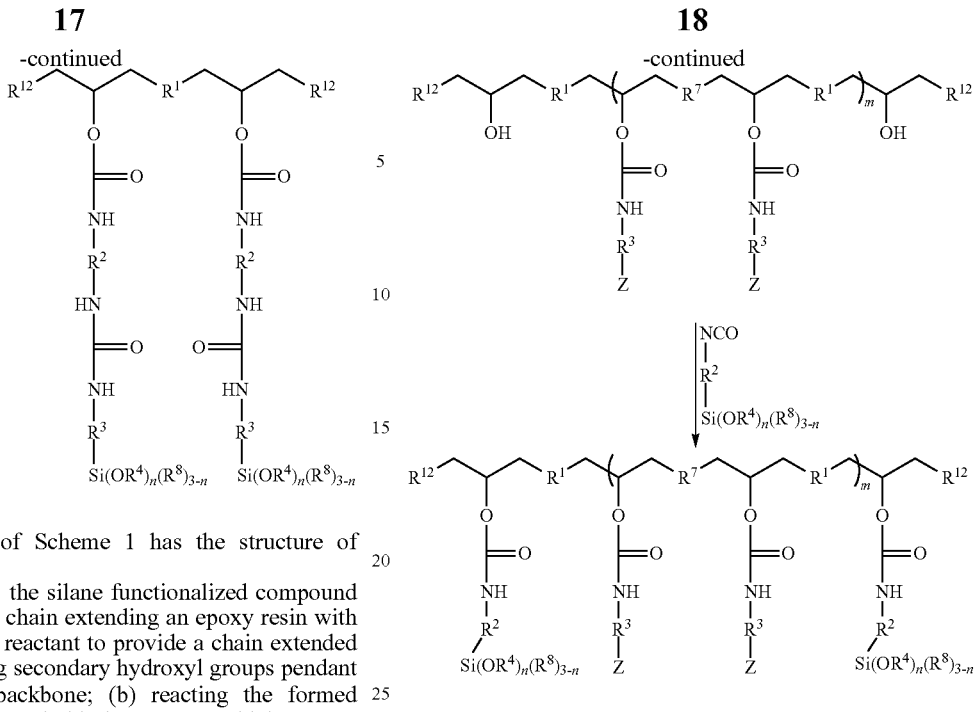

The final product of Scheme 1 has the structure of Formula 5.

In one embodiment, the silane functionalized compound may be formed by: (a) chain extending an epoxy resin with a suitable bifunctional reactant to provide a chain extended epoxy resin comprising secondary hydroxyl groups pendant to the epoxy resin backbone; (b) reacting the formed hydroxyl groups with a suitable isocyanate, which may or may not contain silane; (c) opening the terminal epoxy groups with a suitable functional group, and (d) functionalizing the formed hydroxyl groups with silane containing isocyanate.

In one embodiment, the sequence may be stopped after step (b) to provide an epoxy terminated structure; in this case silane containing isocyanate is used in the step (b). In another embodiment, non-silylated isocyanate is used in the step (b), the product is end-capped with a suitable amine, and the silane containing isocyanate is used on the last step. The process is illustrated by the Scheme 3. The final product of Scheme 3 has the structure of Formula 3.

Scheme 3

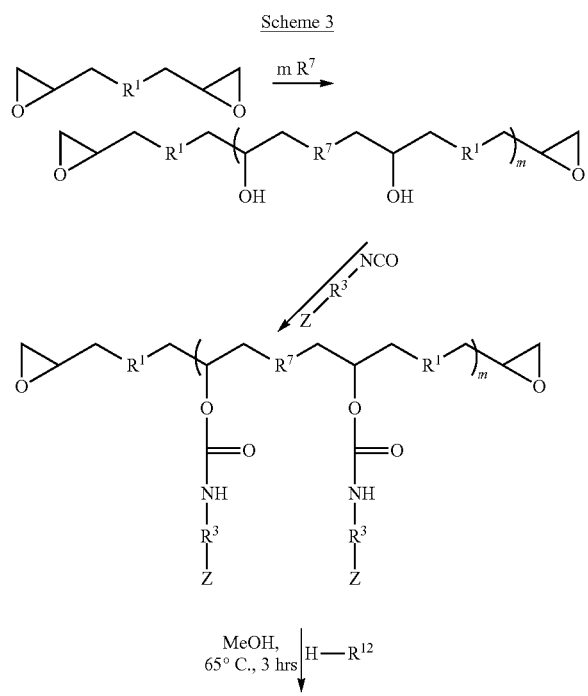

Compositions

The silane functionalized compounds of the invention may be employed in a composition. In one embodiment, the composition comprises: (a) a silane functionalized compound in accordance with aspects of the present invention, and optionally, a (b) catalyst, a (c) polymeric resin, or both.

The compositions may contain the (a) silane functionalized compound in an amount of from about 5 weight percent to about 80 weight percent; from about 5 weight percent to about 50 weight percent; even from about 10 weight percent to about 25 weight percent.

The catalyst material is not particularly limited and may be chose as desired for a particular purpose or intended use. In one embodiment, the catalyst for use with silane functionalized compounds may comprise a metal organic compound. Examples of such catalysts include, but are not limited to, tetraalkyl titanates such as tetraorthobutyl titanate; dialkyltin oxide; dialkyltin oxide hydroxide; aluminium alkoxides; zinc oxide; stannous oxide; dibutyltin oxide; butyltin oxide hydroxide; tetraalkyl tin, such as dibutyltin dilaurate; calcium phosphonate; lithium chloride; zinc acetate dehydrate; zinc undecylenate; calcium acetate monohydrate, and combinations thereof, or any combination or subset thereof.

If the (b) catalyst is present, the composition may contain the (b) catalyst in an amount of from about 0.01 weight percent to about 10 weight percent; from about 0.1 weight percent to about 5 weight percent; for example, from about 0.5 weight percent to about 1 weight percent.

Polymeric resin materials (c) may be included into the composition as desired for a particular purpose or intended use. Non-limiting examples of suitable resins include amine resins, epoxy resins, polydimethylsiloxane resins, acrylic resins, other organo-functionalized polysiloxane resins, polyimide resins, fluorocarbon resins, benzocyclobutene resins, fluorinated polyallyl ethers, polyamide resins, polyimidoamide resins, phenol cresol resins, aromatic polyester resins, polyphenylene ether (PPE) resins, bismaleimide resins, fluororesins, mixtures and hybrids thereof and any other polymeric systems known to those skilled in the art. Amine and amino resins are those resins that comprise at least one amine substituent group on any part of the resin backbone. Amine and amino resins are also synthetic resins derived from the reaction of urea, thiourea, melamine or allied compounds with aldehydes, particularly formaldehyde. Epoxy resins may be any epoxy resin.

If the optional (c) polymeric resin is present, the composition may contain the (c) polymeric resin in an amount of from about 10 weight percent to about 50 weight percent; from about 15 weight percent to about 40 weight percent; even from about 20 weight percent to about 30 weight percent. Here as elsewhere in the specification and claims, numerical values may be combined to form new and non-disclosed ranges. The total weight percent for components (a)-(c) in any composition is 100 weight percent, and the components' weight percent may be modified by the addition of other components, such as solvents.

In one embodiment, the silane functionalized compounds of the invention may be employed in an epoxy resin composition. In one embodiment, an epoxy resin composition comprises: (a) a silane functionalized compound in accordance with aspects of the present invention, an (b) epoxy resin, and, optionally, a (c) epoxy curing agent (or referred to as an epoxy hardener), a (d) catalyst, or both. The epoxy resin may be same the epoxy resins described herein useful in preparing the silane functionalized compounds of the invention.

The epoxy resin composition may contain the (a) silane functionalized compound in an amount of from about 5 weight percent to about 80 weight percent; from about 5 weight percent to about 50 weight percent; even from about 10 weight percent to about 25 weight percent.

The epoxy resin composition may contain the (b) epoxy resin in an amount of from about 10 weight percent to about 50 weight percent; from about 15 weight percent to about 40 weight percent; even from about 20 weight percent to about 30 weight percent. Here as elsewhere in the specification and claims, numerical values may be combined to form new and non-disclosed ranges. The total weight percent for components (a)-(d) in any composition is 100 weight percent, and the components' weight percent may be modified by the addition of other components, such as solvents.

If the (c) epoxy curing agent is present, the composition may contain the (c) curing agent amine curing agent in a molar ratio of epoxy curing agent to epoxy of from about 0.1 to about 2; from about 0.2 to about 0.8; even from about 0.3 to about 0.7.

If the (d) catalyst is present, the composition may contain the (d) catalyst in an amount of from about 0.01 weight percent to about 10 weight percent; from about 0.1 weight percent to about 5 weight percent; for example, from about 0.5 weight percent to about 1 weight percent. The (d) catalyst is the same catalyst as described as (b) catalyst herein.

The (c) epoxy curing agent (or curing agent) is not particularly limited and may be selected as desired for a particular purpose or end use. In one embodiment, the curing agents utilized in the compositions include amine- and amide-containing curing agents having one or more active hydrogen atoms. The active hydrogen atoms may be bonded to the same nitrogen atom or to different nitrogen atoms. Examples of suitable curing agents include those compounds that contain a primary amine moiety, and compounds that contain two or more primary or secondary amine or amide moieties linked to a common central organic moiety. Examples of suitable amine-containing curing agents include ethylene diamine, diethylene triamine, polyoxypropylene diamine, triethylene tetramine, dicyandiamide, melamine, cyclohexylamine, benzylamine, diethylaniline, methylenedianiline, m-phenylenediamine, diaminodiphenylsulfone, 2,4 bis(p-aminobenzyl)aniline, piperidine, N,N-diethyl-1,3-propane diamine, and the like, and soluble adducts of amines and polyepoxides and their salts, such as described in U.S. Pat. Nos. 2,651,589 and 2,640,037.

In another embodiment, polyamidoamines may be utilized as a curing agent in the resin compositions. Polyamidoamines are typically the reaction product of a polyacid and an amine. Examples of polyacids used in making these polyamidoamines include 1,10-decanedioic acid, 1,12-dodecanedioic acid, 1,20-eicosanedioic acid, 1,14-tetradecanedioic acid, 1,18-octadecanedioic acid and dimerized and trimerized fatty acids. Amines used in making the polyamidoamines include aliphatic and cycloaliphatic polyamines such as ethylene diamine, diethylene triamine, triethylene tetramine, tetraethylene pentamine, 1,4-diaminobutane, 1,3-diaminobutane, hexamethylene diamine, 3-(N-isopropylamino)propylamine and the like. In another embodiment, polyamides are those derived from the aliphatic polyamines containing no more than 12 carbon atoms and polymeric fatty acids obtained by dimerizing and/or trimerizing ethylenically unsaturated fatty acids containing up to 25 carbon atoms.

In another embodiment, the curing agents are aliphatic polyamines, polyglycoldiamines, polyoxypropylene diamines, polyoxypropylenetriamines, amidoamines, imidazoles, reactive polyamides, ketimines, araliphatic polyamines (i.e. xylylenediamine), cycloaliphatic amines (i.e. isophoronediamine or diaminocyclohexane), menthane diamine, 4,4-diamino-3,3-dimethyldicyclohexylmethane, heterocyclic amines (aminoethyl piperazine), aromatic polyamines (methylene dianiline), diamino diphenyl sulfone, mannich base, phenalkamine, N,N',N"-tris(6-aminohexyl) melamine, and the like. In another embodiment, imidazoles, which may be utilized as an accelerator for a curing agent, may also be utilized as a curing agent.

In another embodiment, the curing agent is a phenolic curing agent which includes compounds having an average of one or more phenolic groups per molecule. Suitable phenol curing agents include dihydroxy phenols, biphenols, bisphenols, halogenated biphenols, halogenated bisphenols, hydrogenated bisphenols, alkylated biphenols, alkylated bisphenols, trisphenols, phenol-aldehyde resins, phenol-aldehyde novolac resins, halogenated phenol-aldehyde novolac resins, substituted phenol-aldehyde novolac resins, phenol-hydrocarbon resins, substituted phenol-hydrocarbon resins, phenol-hydroxybenzaldehyde resins, alkylated phenol-hydroxybenzaldehyde resins, hydrocarbon-phenol resins, hydrocarbon-halogenated phenol resins, hydrocarbon-alkylated phenol resins, or combinations thereof. Preferably, the phenolic curing agent includes substituted or unsubstituted phenols, biphenols, bisphenols, novolacs or combinations thereof.

In another embodiment, the curing agent is a polybasic acid or its corresponding anhydride. Examples of polybasic acids include di-, tri-, and higher carboxylic acids, such as, oxalic acid, phthalic acid, terephthalic acid, succinic acid, alkyl and alkenyl-substituted succinic acids and tartaric acid. Examples also include polymerized unsaturated acids, for example, those containing at least 10 carbon atoms, and preferably more than 14 carbon atoms, such as, dodecenedioic acid, and 10,12-eicosadienedioic acid. Examples of suitable anhydrides include phthalic anhydride, succinic anhydride, maleic anhydride, nadic anhydride, nadic methyl anhydride, pyromellitic anhydride, trimellitic anhydride and the like. Other types of acids that are useful are those containing sulfur, nitrogen, phosphorus or halogens; chlorendic acid, benzene phosphonic acid, and sulfonyl dipropionic acid bis(4-carboxyphenyl)amide.

The ratio of curing agent to epoxy resin may be selected to provide a fully cured resin. The amount of curing agent which may be present may vary depending upon the particular curing agent used (due to the cure chemistry and curing agent equivalent weight) as is known in the art.

In the compositions of the invention, the silane functionalized compound, alone or in combination with the curing agent, the catalyst compound, the polymeric resin, and combinations thereof, may optionally be dissolved in a solvent. When the solvent is present, a solution containing the silane functionalized compound may comprise from about 0 to about 50 weight percent of the solvent, such as from 10 to 40 weight percent, for example from about 20 to about 30 weight percent of the solvent in the solution. Preferably the concentration of solids in the solution having the solvent is from about 50 to about 100, such as from about 60 percent to about 90, for example, from about 70 to about 80 percent solids.

Non-limiting examples of suitable solvents include ketones, alcohols, water, glycol ethers, esters, aromatic hydrocarbons and mixtures thereof. Suitable solvents include acetone, methyl ethyl ketone, methyl isobutyl ketone, cyclohexanone, methylpyrrolidinone, propylene glycol monomethyl ether, ethylene glycol monomethyl ether, methyl amyl ketone, ethyl acetate, butyl acetate, methanol, isopropanol, toluene, xylene, dimethylformamide (DMF) and the like. A single solvent may be used, but also separate solvents may be used for one or more components. Suitable solvents for the epoxy resins include, but are not limited to, ketones, including acetone, methylethyl ketone and the like. Suitable solvents for the curing agents include, for example, ketones, amides such as dimethylformamide (DMF), ether alcohols such as methyl, ethyl, propyl or butyl ethers of ethylene glycol, diethylene glycol, propylene glycol or dipropylene glycol, ethylene glycol monomethyl ether, or 1-methoxy-2-propanol. Suitable solvents for the catalyst include, but are not limited to alcohols, ketones, water, dimethylformamide (DMF), glycol ethers such as propylene glycol monomethyl ether or ethylene glycol monomethyl ether, and combinations thereof.

The resin compositions may also include additional components including, and not limited to inorganic fillers, additional flame retardants, for example antimony oxide, octabromodiphenyl oxide, decabromodiphenyl oxide, dyes, pigments, surfactants, flow control agents, and combinations thereof.

In one aspect, the compositions of the present invention exhibit good properties when cured. In one embodiment, compositions of the present invention have one or more of good flexibility, impact resistance, light stability, and combinations thereof.

Compositions comprising the silane functionalized compounds of the invention may be used in a variety of applications including but not limited to, a coating, an adhesive, a sealant, as a component of a composite material, and combinations thereof. In one embodiment, the compositions may be employed as a primer for a metal surface. In one embodiment, the compositions may be employed as a coating such as an architectural or industrial coating, a pipeline coating, a tank lining, and combinations thereof. In one embodiment, the compositions comprising the silane functionalized compounds of the invention may be employed in an antifouling coating composition. In another embodiment, the compositions may be useful as a structural adhesive.

EXAMPLES

Silane Functionalized Epoxy Derived Resins

Example 1

A silane functionalized epoxy derived resin in accordance with Formula 2 is prepared as follows:

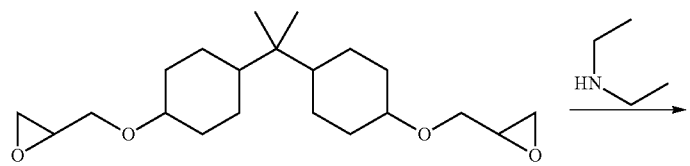

Eponex 1510

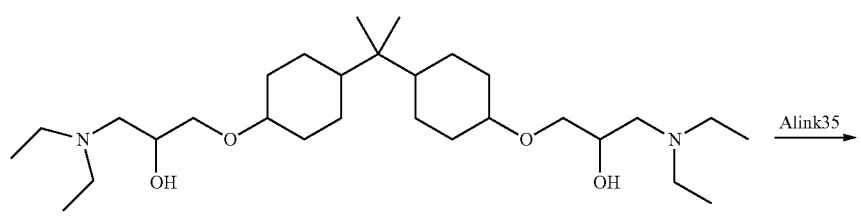

-continued

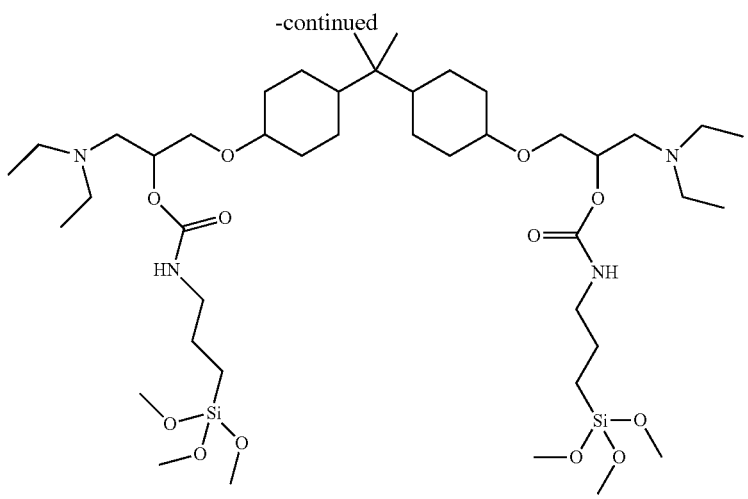

2

Intermediate 1.

420 g, 1 mol, of Eponex 1510 were mixed with 154 g, 2.1 moles of diethylamine and 100 g of methanol in a 4-neck round-bottom flask equipped with a mechanical stirrer, temperature probe, reflux condenser, and a nitrogen inlet. The reaction is exothermic, cooling with an ice bath being necessary to keep the temperature at or below 65-67° C. When exotherm subsided, the reaction temperature was kept at 50° C. with a heating mantle for 4 hours. The reaction was monitored by epoxy titration with and without CTAB (cetyl trimethylammonium bromide). Upon completion, indicated by the same values obtained with and without CTAB, methanol and excess of the amine were removed from the reaction mixture by distillation at 80° C. in the flask, nitrogen streamed through the reaction mixture. To ensure removal of methanol and diethylamine, toluene (2×100 g) was added to the reaction mixture, the temperature was increased to 115° C., and the distillate was analyzed by GC to confirm the absence of methanol and diethylamine. To the intermediate in the reaction flask were added 103 g of ethyl acetate, to lower its viscosity. The intermediate 1, 672 g, contained 13% of residual toluene, determined on moisture analyzer.

Product 2. 254 g of the intermediate 1, 390 mmol, were heated up to 50° C., and 168 g, 2.1 equivalents of isocyanatopropyltrimethoxysilane (A-link 35) were added fast to the stirred reaction mixture, addition funnel rinsed with ethyl acetate (15 ml). The temperature through and after the addition was maintained at or below 70° C.; occasional cooling was necessary. When the exotherm subsided, the reaction mixture was held for 2 hours at 70° C. and then sampled for FTIR which showed no residual isocyanate at 2270 cm$^{-1}$, and a carbonyl peak at 1690-1720 cm$^{-1}$. LC/MS analysis showed the presence of target mass 910 (m/z H+, doubly charged) in the main peak. The product 2, 424 g, was transferred into a jar with PFTE lined cap, surface swept with nitrogen. Solvent content by moisture analyzer 15.6%.

In a similar manner, using diethylamine and A-link 25, was obtained Product 3 FTIR: carbonyl peak at 1690-1720 cm$^{-1}$. LC/MS: target mass 994 (m/z H+, doubly charged) in the main peak.

In a similar manner, using dibutylamine and A-link 35, was obtained Product 4. FTIR: carbonyl peak at 1690-1720 cm$^{-1}$. LC/MS: target mass 1022 (m/z H+, doubly charged) in the main peak.

In a similar manner, using morpholine and A-link 35, was obtained Product 5. FTIR: carbonyl peak at 1690-1720 cm$^{-1}$. LC/MS: target mass 937 (m/z H+) in the main peak.

In a similar manner, using diethanolamine and 2-(methylamino)ethanol and adjusting the amount of A-link 35, were obtained Products 6 (FTIR: carbonyl peak at 1690-1720 cm$^{-1}$. LC/MS: target mass 1323 (m/z H+, doubly charged) in the main peak) and 7 (FTIR: carbonyl peak at 1690-1720 cm$^{-1}$. LC/MS: target mass 1794 (m/z H+, doubly charged).

In a similar manner, using EPON™ 828, diethylamine, and A-link 35, was obtained Product 8. FTIR: carbonyl peak at 1690-1720 cm$^{-1}$. LC/MS: target mass 898 (m/z H+, doubly charged) in the main peak.

Example 2
A silane functionalized epoxy derived resin in accordance with Formula 2 is prepared as follows:
Example 3
A silane functionalized epoxy derived resin in accordance with Formula 3 is prepared as follows:
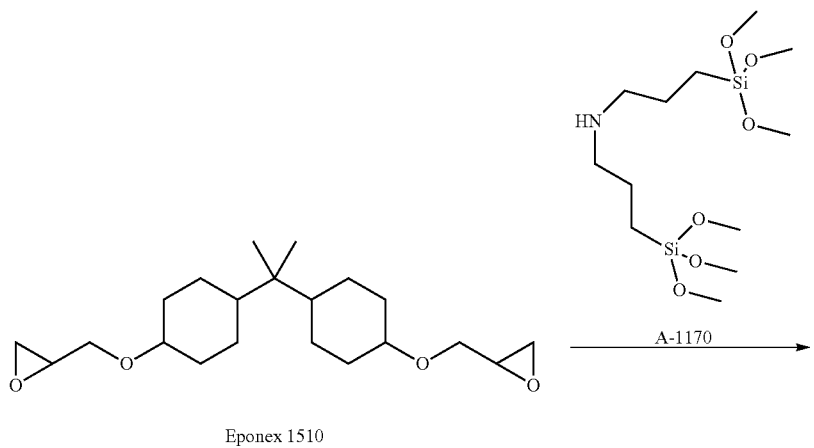
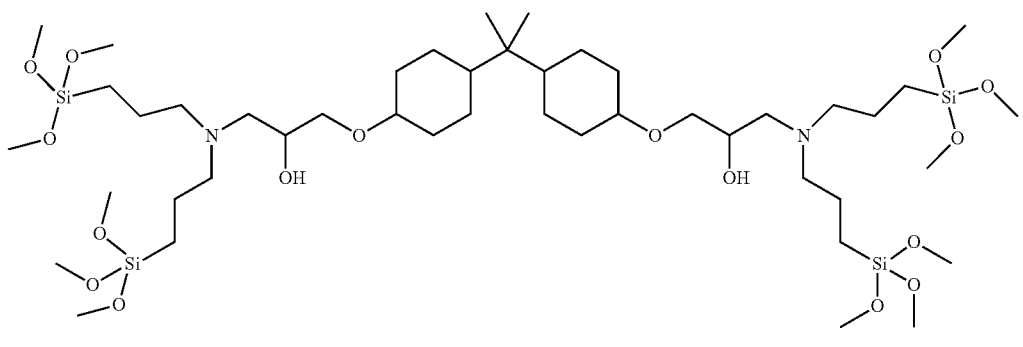
9
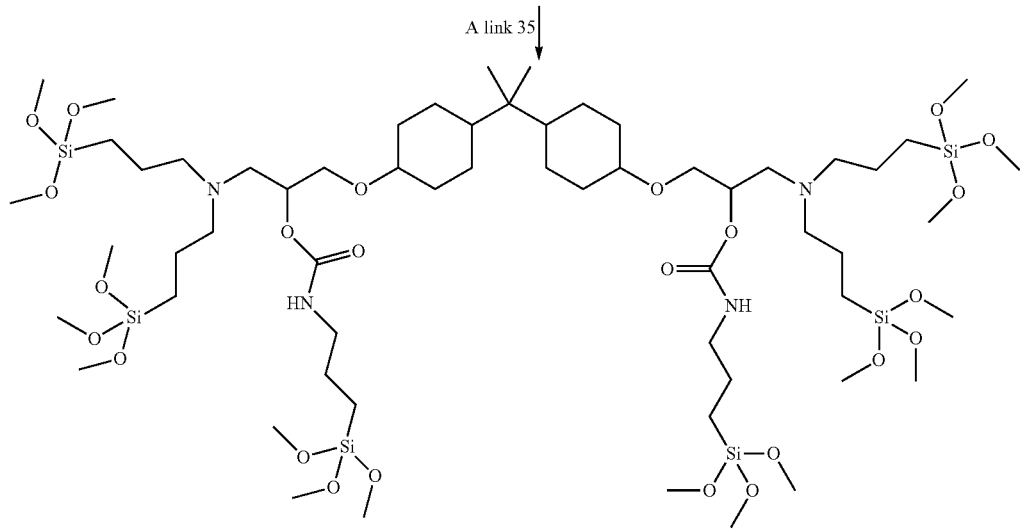
10

Eponex 1510 (40.9 g, 100 mmol) and amine A-1170 (78 g, 230 mmol) were mixed with an overhead stirrer in a 0.5 L 4-neck round bottom flask, equipped with a thermometer, reflux condenser, addition funnel, nitrogen inlet. The flask was immersed into an oil bath, preheated to 65° C., and the reaction was stirred at that temperature for 4 hours, and for one more hour at 76° C. in the bath. Epoxy ring opening was monitored by titration with and without CTAB reagent. A-link 35 (41.6 g, 200 mmol) was added to the resulting mixture at 75-78° C. over 20 minutes. Brief exotherm to 90° C. was observed. The resulting reaction mixture was stirred at 80° C. for an hour, and at 90° C. for one more hour, until FTIR analysis showed no residual isocyanate at 2270 cm$^{-1}$. To the resulting clear viscous mixture was added methanol (70 g), and it was allowed to cool down to room temperature under nitrogen overnight. 220 g of the product 10 were stored in a jar with PFTE lined cap, surface swept with nitrogen. FTIR: carbonyl peak at 1690-1720 cm$^{-1}$. LC/MS: target mass 1446 (m/z H+, doubly charged) in the main peak.

In a similar manner, using A-1170 and ethyl isocyanate, was obtained Product 11.

In a similar manner, using A-link 15 and A-link 35, was obtained Product 12.

In a similar manner, using A-link 15 and ethyl isocyanate, was obtained Product 13.

Example 4

A silane functionalized epoxy derived resin in accordance with Formula 3 prepared as follows;

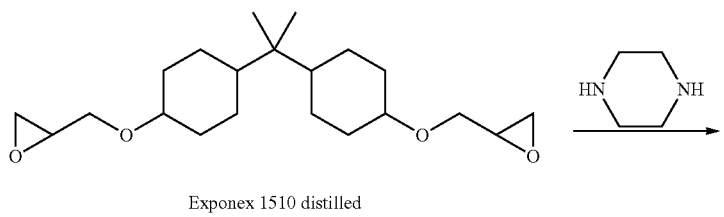

Exponex 1510 distilled

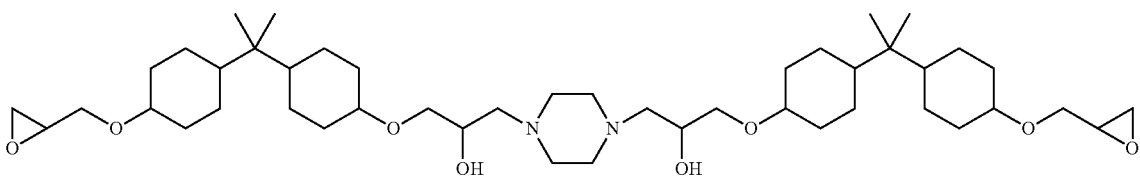

14

| ethyl isocyanate

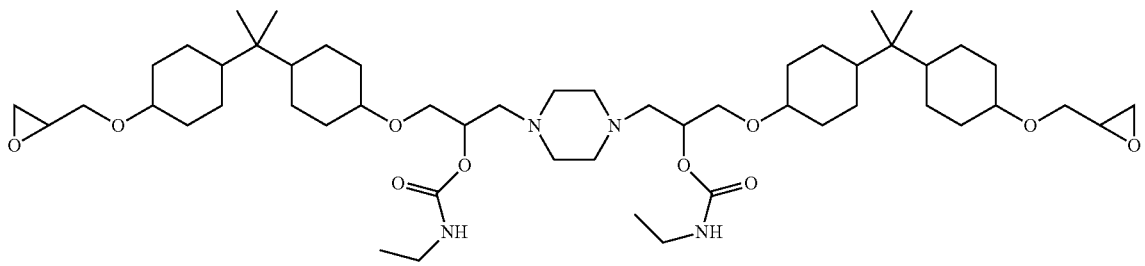

15

| diethylamine

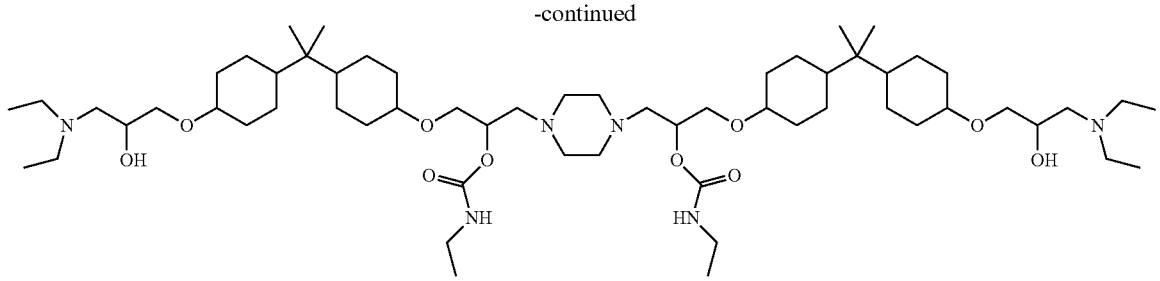

16

↓ A link 35

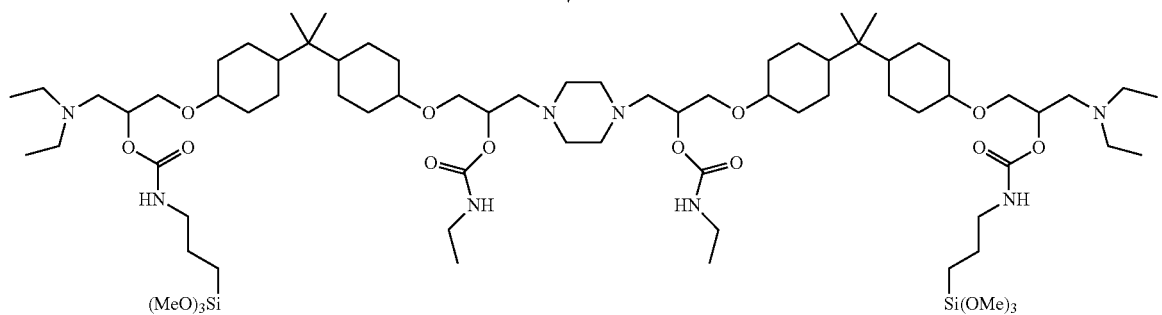

17

Eponex 1510 distilled (35.2 g, 100 mol), and methanol (30 g) were mixed in a 4-neck round-bottom flask equipped with a mechanical stirrer, temperature probe, reflux condenser, and a nitrogen inlet. To the mixture was added piperazine (4.3 g, 50 mmol), and the resulting solution was stirred at 50° C. for 2 hours. Methanol was removed from the reaction mixture by distillation at 80° C. in the flask, nitrogen streamed through the reaction mixture. To ensure removal of methanol, toluene (2×30 g) was added to the reaction mixture, and distilled off. To the intermediate 14 was added ethyl isocyanate (7.8 g, 110 mmol) at 55° C., and the resulting mixture was stirred at 50° C. for 20 hours and then sampled for FTIR. Analysis showed no residual isocyanate at 2270 cm$^{-1}$, which indicated formation of the intermediate 15, a thick yellow gum. To the intermediate 15 were added methanol (50 g) and diethylamine (10.5 g, 143 mmol), and the resulting mixture was stirred at 50° C. for 24 hours. Upon completion, indicated by the same values obtained by titration with and without CTAB, methanol and excess of the amine were removed from the reaction mixture by distillation at 80° C. in the flask, nitrogen streamed through the reaction mixture. To ensure removal of methanol, toluene (2×30 g) was added to the reaction mixture, and distilled off. To the formed intermediate 16 were added 40 g of toluene and 20.5 g, 100 mmol, of isocyanatopropyltrimethoxysilane (A-link 35) at 66-70° C. The temperature through and after the addition was maintained at or below 70° C.; occasional cooling was necessary. When the exotherm subsided, the reaction mixture was held for 2 hours at 70° C. and then sampled for FTIR which showed no residual isocyanate at 2270 cm$^{-1}$. To the product 17 were added 10 g of methanol, and it was transferred into a jar with PETE lined cap, surface swept with nitrogen.

Example 5

A silane functionalized epoxy derived resin in accordance with Formula 4 is prepared as follows;

Intermediate 18

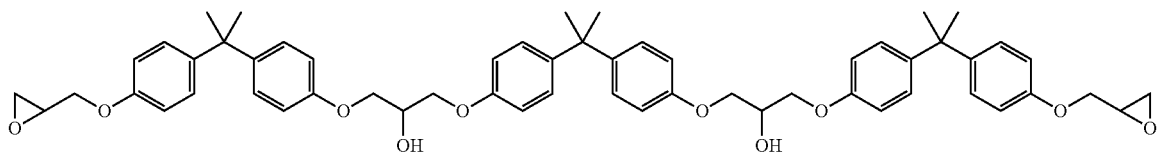

Epon 1001 × 75

↓ Phenyl isocyanate

-continued

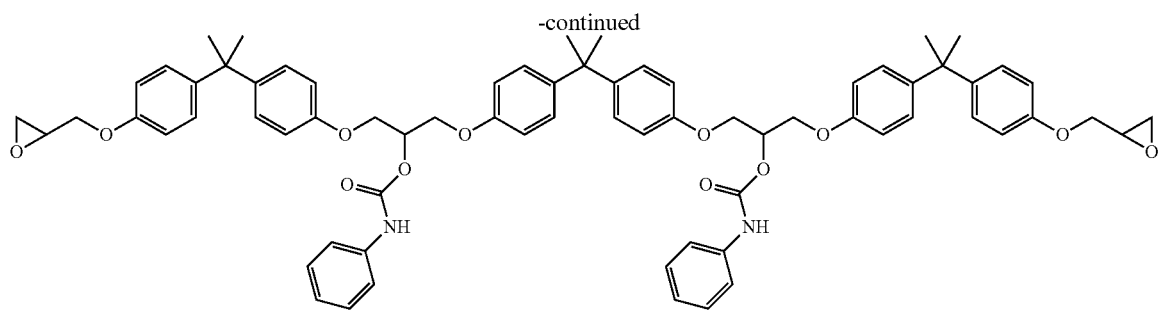

18

Into a 1 L ml 4-neck round-bottom flask equipped with a mechanical stirrer, temperature probe, reflux condenser, and a nitrogen inlet were placed 460 g, 780 mmol of epoxy, of EPON™ 1001×75 resin. The resin was heated up to 75° C. with stirring, and to it were added 92 g, 780 mmol, of phenyl isocyanate. The temperature during and after addition was maintained at or below 80° C. (occasional cooling necessary). After the addition was complete, the reaction mixture was stirred at 75° C. until FTIR showed no residual isocyanate at 2270 cm$^{-1}$ (about 2 hours). To the resulting light-yellow viscous liquid were added 30 g of xylenes and 100 g of toluene to lower viscosity. The intermediate 18 was characterized by epoxy equivalent weight, 860, and solvent content, 29.5%.

Product 20

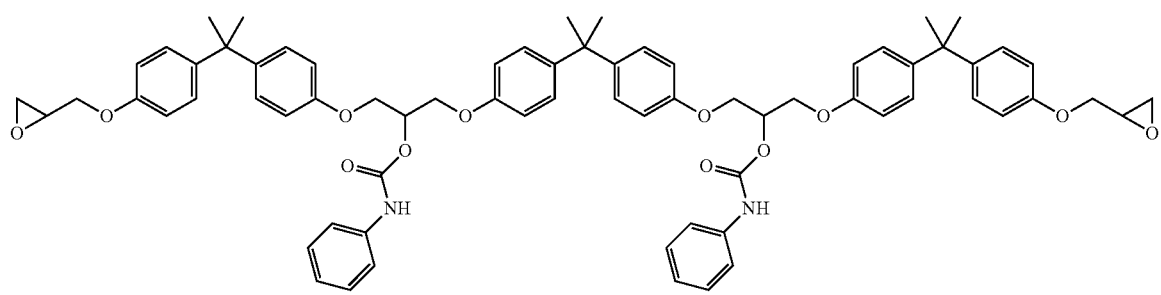

18

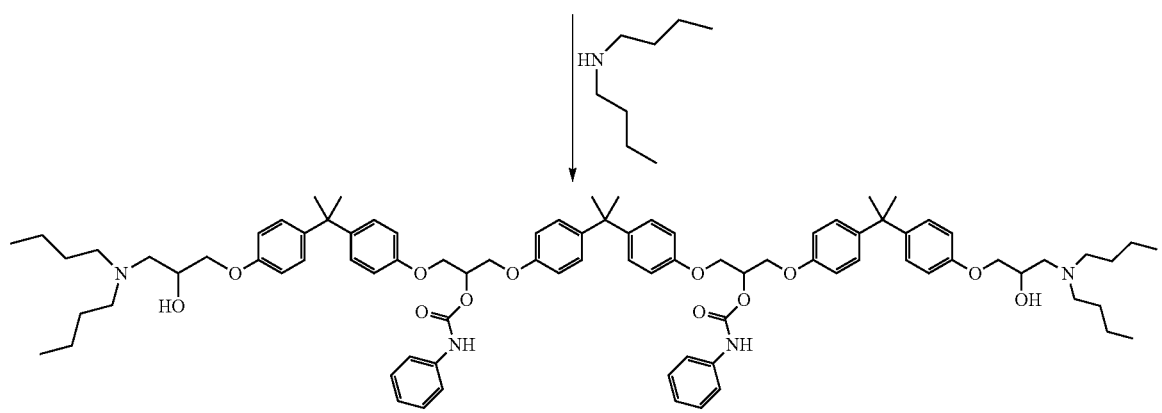

19

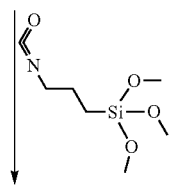

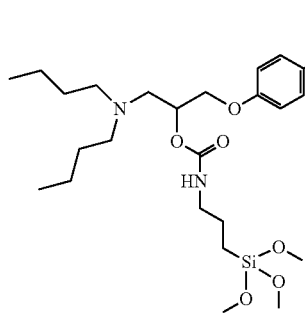
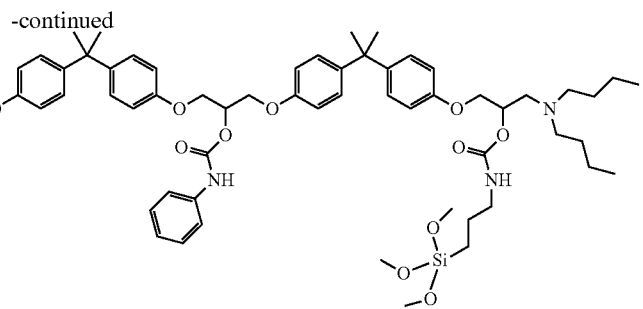

-continued

A mixture of intermediate 18 (215 g, 250 mmol), di-n-butylamine (35 g, 275 mmol), and methanol (30 g) was heated up to 70° C. and stirred at that temperature for 5 hours. The reaction was monitored by epoxy titration with and without CTAB. Upon completion, indicated by the same values obtained with and without CTAB, methanol was distilled off the reaction mixture at 115° C. in the flask, nitrogen streamed through the reaction mixture. To ensure removal of methanol, toluene (100 g) was added to the reaction mixture and distilled off. To the formed intermediate 19 were added 56.4 g, 275 mmol, of isocyanatopropyltrimethoxysilane (A-link 35) at 66-70° C. When the exotherm subsided, the reaction mixture was held for 10 hours at 50° C. and then sampled for FTIR which showed no residual isocyanate at 2270 $cm^{-1}$. To the product 20 were added 30 g of NBA, and it was transferred into a jar with PFTE lined cap, surface swept with nitrogen. Yield 427 g, solvent content 37.0%.

In a similar manner, using diethanolamine and 2-(methylamino)ethanol instead of dibutylamine and adjusting the amount of A-link 35, were obtained Products 21 and 22.

Example 5

A silane functionalized epoxy deviated resin in accordance with Formula 4 is prepared as follows:

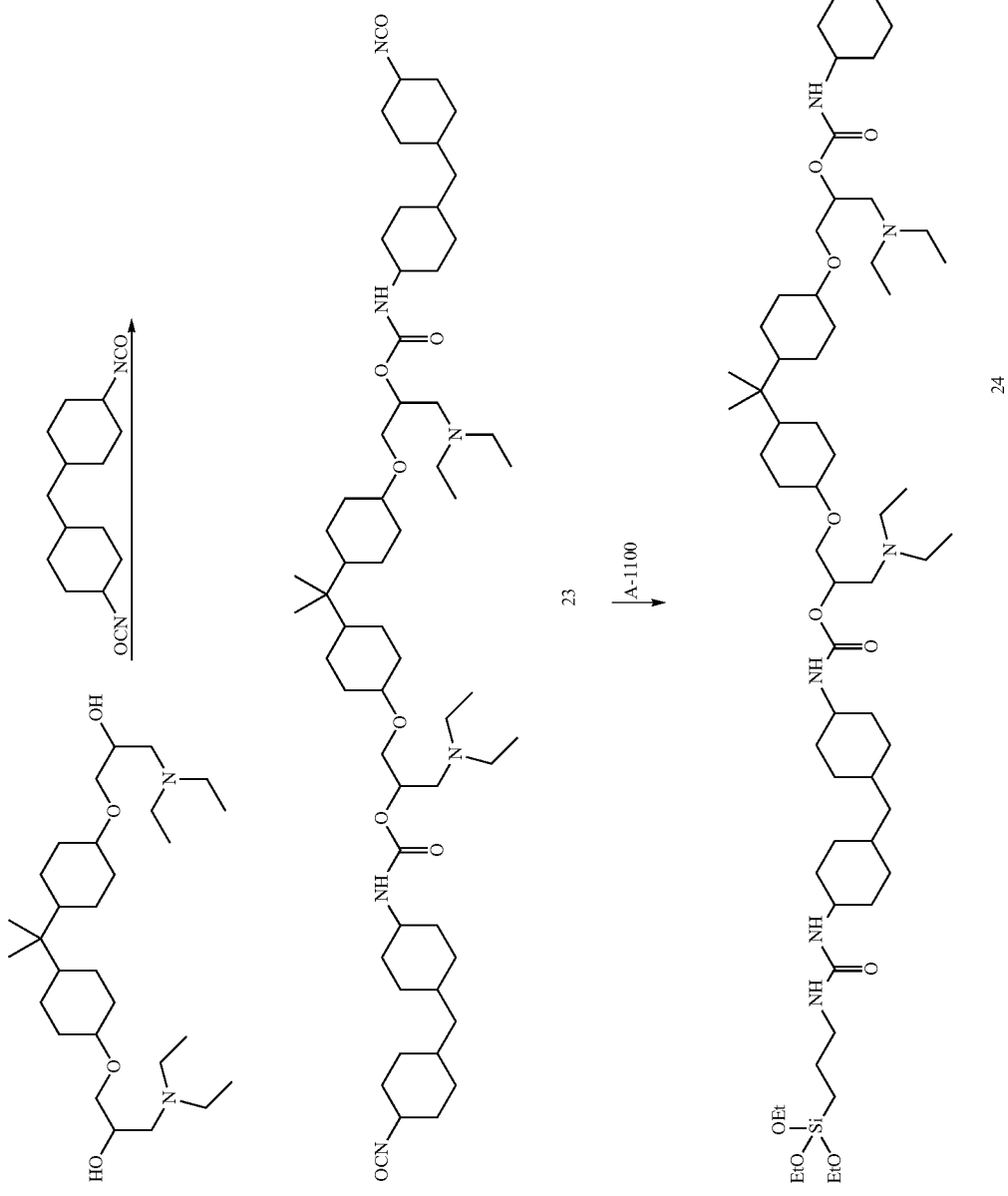

Into a 500 ml 4-neck round-bottom flask equipped with a mechanical stirrer, temperature probe, reflux condenser, and a nitrogen inlet were placed 63 g, 240 mmol, of 4,4'-methylenebis(cyclohexyl isocyanate) and 30 g of n-butyl acetate (NBA). The mixture was warmed up to 50° C., and to it were added 78.4 g, 120 mmol, of intermediate 1 (Mw 566 by the amino content, 13% ethyl acetate by moisture analyzer). The resulting mixture was stirred at 50° C. for 20 hours, becoming very viscous; then 30 g of NBA were added, and the reaction mixture was stirred at 70° C. for 2 hours. The resulting intermediate 22, yellow viscous liquid, was cooled to the ambient temperature, and to it were added 54 g, 240 mmol, of aminopropyltriethoxysilane (A-1100). The addition was very exothermic; to keep the temperature below 50° C., cooling with the ice bath was necessary. The resulting mixture, very viscous, was diluted with 90 g of NBA and sampled for FTIR which showed no residual isocyanate at 2270 $cm^{-1}$. The product 24, 355 g, was transferred into a jar with PFTE lined cap, surface swept with nitrogen. Solvent content 48% by the moisture analyzer.

Example 6

A silane functionalized epoxy derived resin in accordance with Formula 3 is prepared as follows;

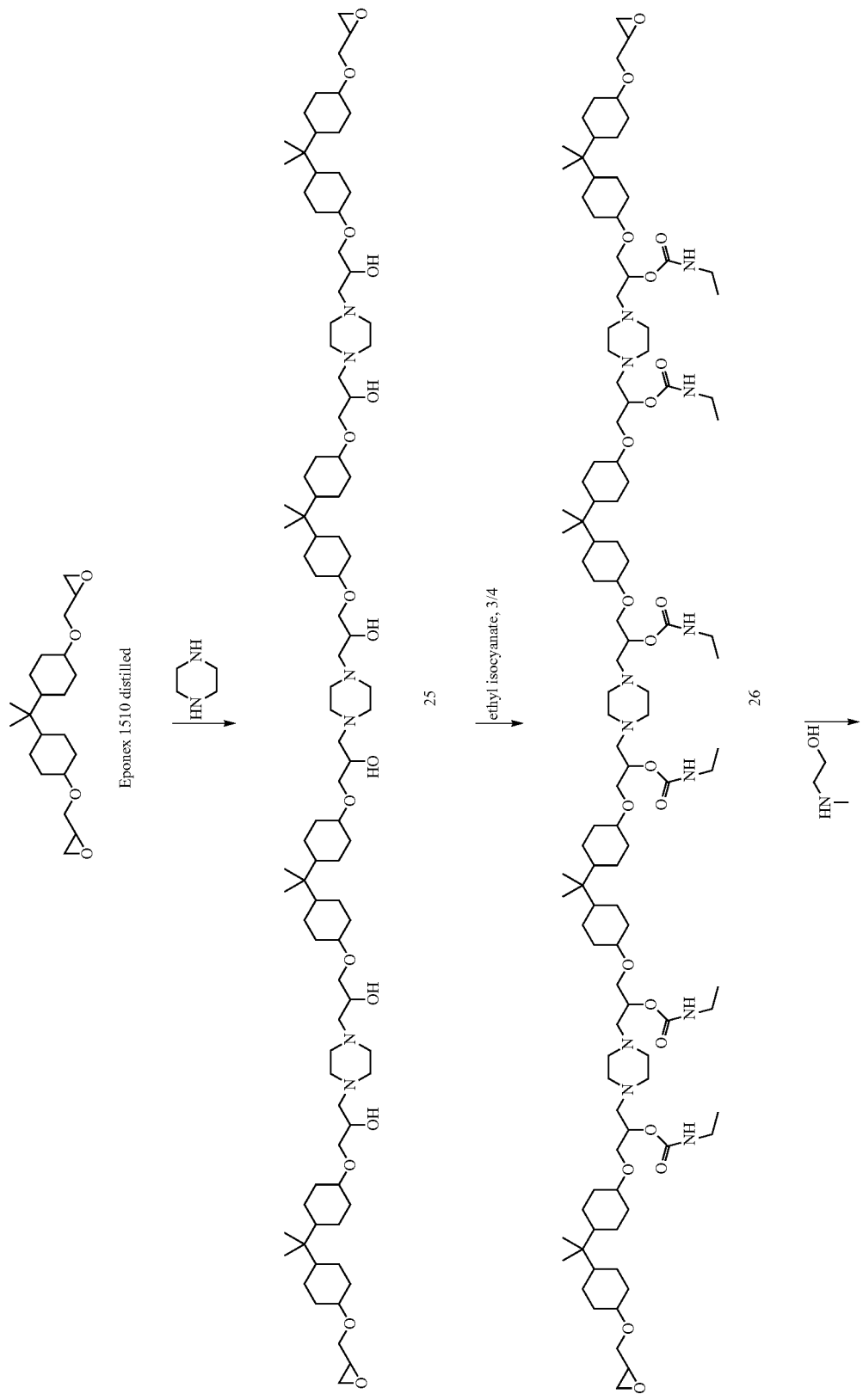

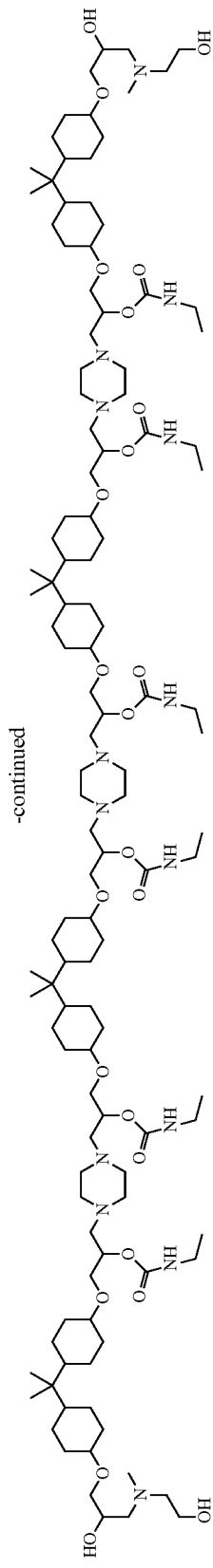
27
↓ A link 35
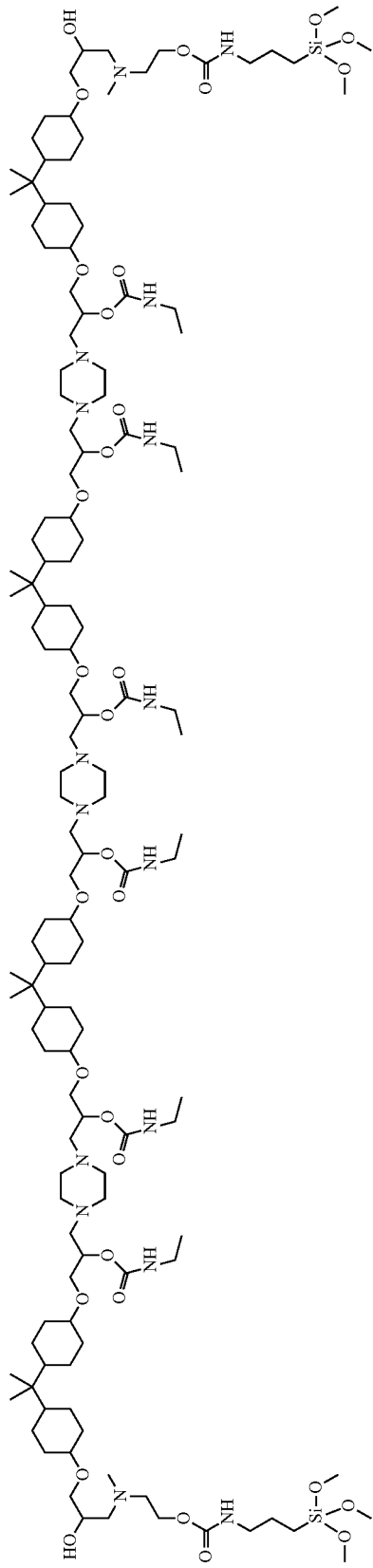
28
↓ ethyl isocyanate, 1/4

-continued
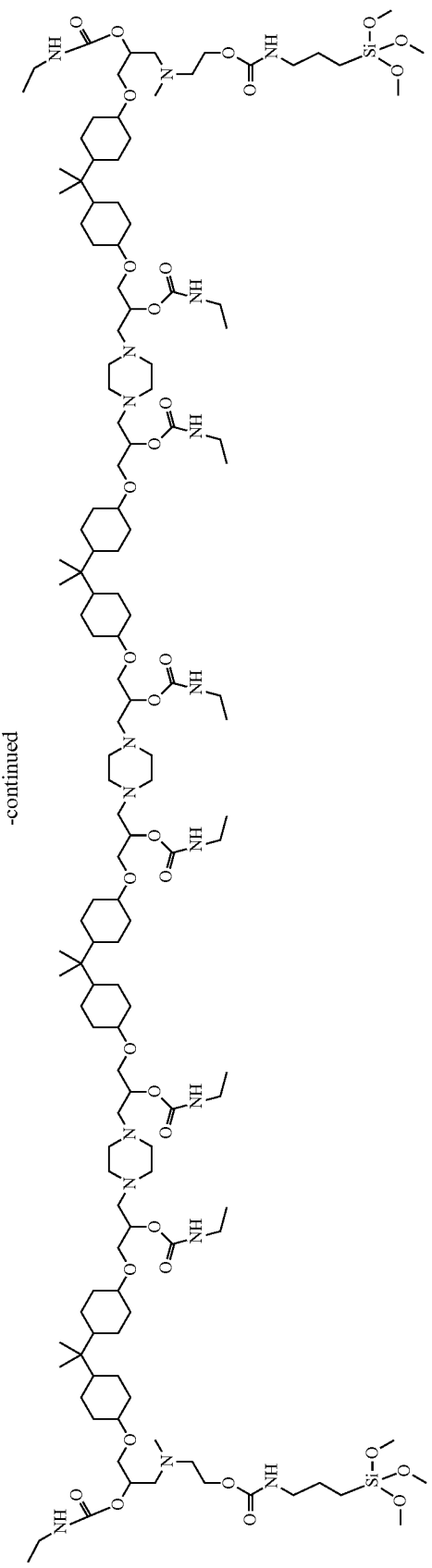
29

Eponex 1510 distilled (35.2 g, 100 mol), and a solution of piperazine (6.5 g, 75 mmol) in methanol (16 g) were mixed up in a 4-neck round-bottom flask equipped with a mechanical stirrer, temperature probe, reflux condenser, and a nitrogen inlet. The resulting solution was stirred at 65° C. for 1 hour. Toluene, 50 g, was added to the reaction mixture, the temperature was increased to 105° C., and methanol was distilled off, with nitrogen streamed through the reaction mixture. The removal of methanol was monitored by 1H NMR, which showed gradual disappearance of the signal at 3.4 ppm, corresponding to methoxy group. To the intermediate 25 was added ethyl isocyanate (10.6 g, 150 mmol) at 55° C. via syringe, and the resulting mixture was stirred at 50° C. for 30 hours and then sampled for FTIR. Analysis showed no residual isocyanate at 2270 $cm^{-1}$, which indicated formation of the intermediate 26, a thick yellow gum. To the intermediate 26 was added 2-(methylamino)ethanol (4.0 g, 53 mmol), and the resulting mixture was stirred at 70° C. for 3 hours. Upon completion, indicated by the same values obtained by titration with and without CTAB, to the formed intermediate 27 was isocyanatopropyltrimethoxysilane (A-link 35) (10.2 g, 50 mmol) at 59-60° C. The temperature through and after the addition was maintained at or below 60° C.; occasional cooling was necessary. After the addition of A-link 35 was over, the reaction temperature was lowered to 50-52° C., and ethyl isocyanate (3.6 g, 50 mmol) was added via syringe. Exotherm to 55° C. was observed. When the exotherm subsided, the reaction mixture was held for 2 hours at 55° C. and at room temperature for 16 hours. The reaction mixture was sampled for FTIR which showed no residual isocyanate at 2270 $cm^{-1}$. To the product 29 were added 11 g of toluene, and it was transferred into a jar with PFTE lined cap, surface swept with nitrogen. Yield 111 g, 37% of toluene in the product.

Example 7

A silane functionalized epoxy derived resin in accordance with Formula 3 is prepared as follows;

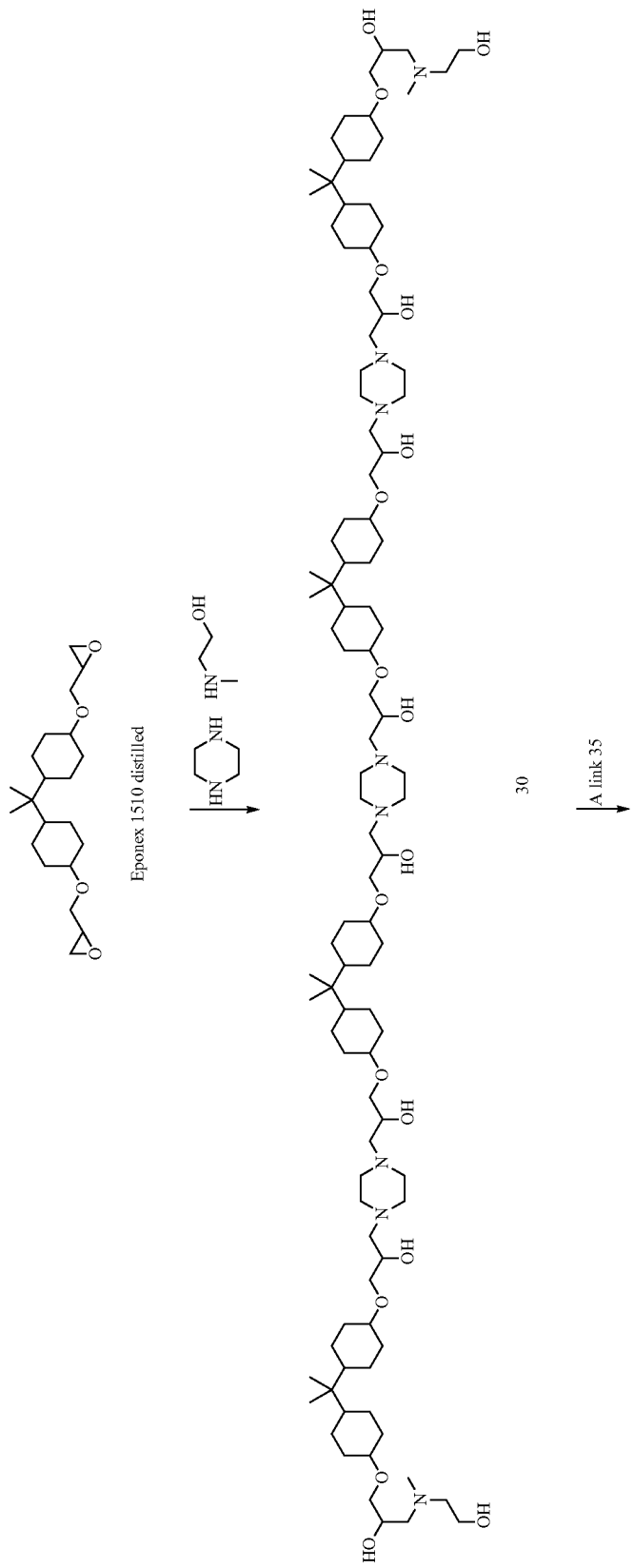

-continued
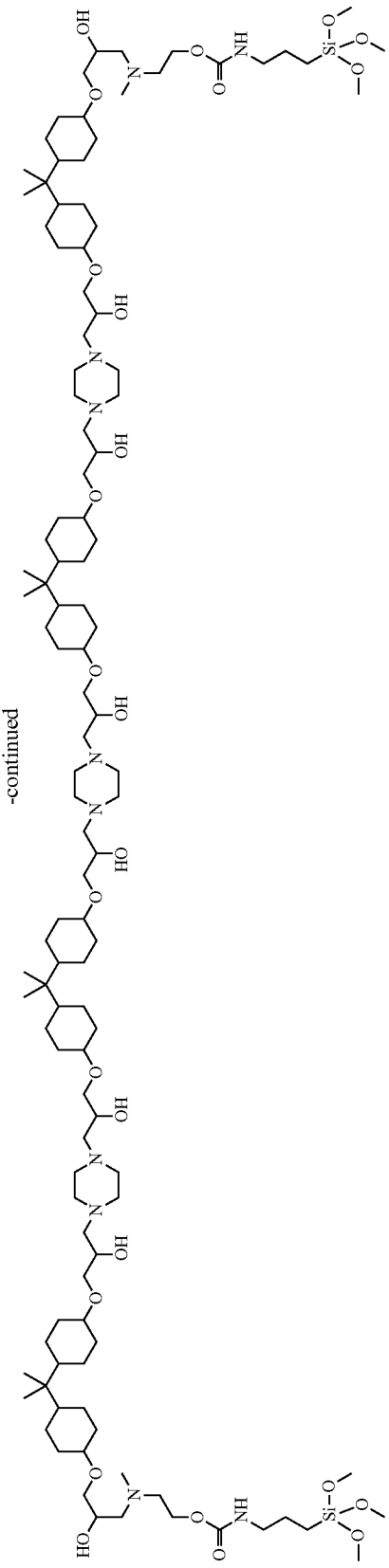
31
↓ ethyl isocyanate
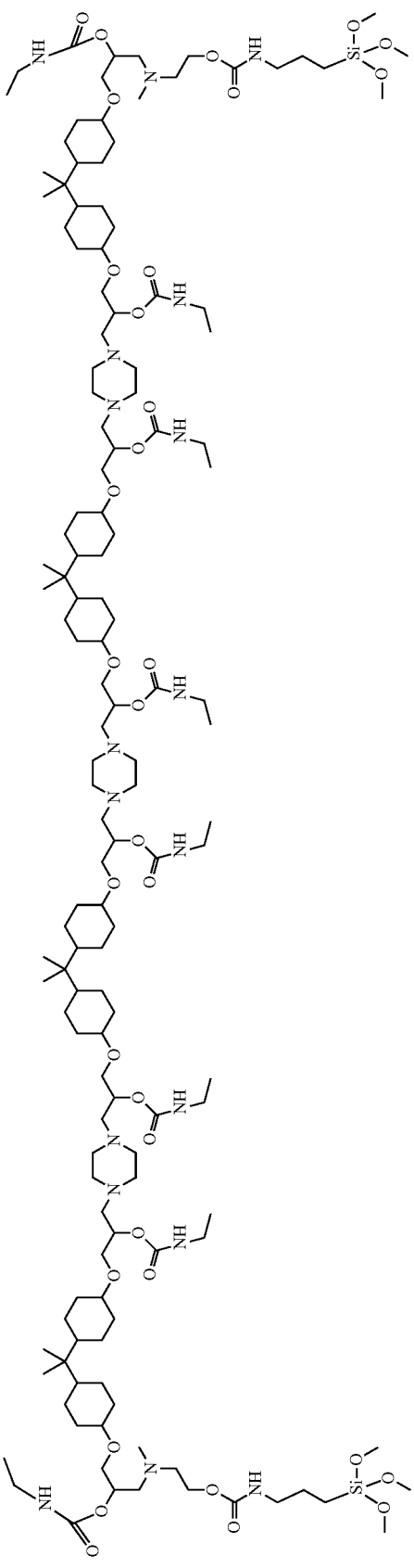
32

Eponex 1510 distilled (35.2 g, 100 mol), piperazine (6.5 g, 75 mmol), 2-(methylamino)ethanol (4.0 g, 53 mmol), and toluene (25 g) were mixed up in a 4-neck round-bottom flask equipped with a mechanical stirrer, temperature probe, reflux condenser, and a nitrogen inlet. The resulting solution was stirred at 65° C. for 24 hours and monitored by titration with and without CTAB to confirm complete conversion of the epoxy groups and forming of the intermediate 30. To the intermediate 30, light-yellow, very viscous, were added 21 g of toluene, temperature in the reaction lowered to 46° C., and A-link 35 added to the reaction at that temperature. No significant exotherm was observed. After stirring at 50° C. for 1 hour, to the reaction was added ethyl isocyanate (124.2 g, 200 mmol) via syringe at 50° C. The resulting mixture was stirred at 55° C. for 30 hours and then sampled for FTIR. Analysis showed no residual isocyanate at 2270 $cm^{-1}$, which indicated formation of the product 32. It was transferred into a jar with PFTE lined cap, surface swept with nitrogen. Yield 104 g, 33% of toluene in the product.

The Resin products were then applied to substrate and tested as shown below. For the data below, the following information is detailed.

König Pendulum Hardness: König Hardness was collected using a BYK Gardner pendulum hardness tester using a König pendulum. Data was collected either using a 12° to 3° or the traditional 6° to 3° amplitude.

Delta E: Delta E data was collected using a Konica Minolta CR-400 chroma meter using L*a*b* color space.

Gloss 60 degree: Gloss was measured using a BYK Gardner micro trigloss and 60° data reported.

Viscosity: Viscosity was recorded using a Brookfield viscometer with the instrument type and spindle noted next to data.

Pencil Hardness: Pencil hardness data was collected according to ASTM 3363.

Forward Impact Resistance (in-lbs): Forward impact resistance data was collected using a BYK Gardner impact tester. Failure of the coating was determined by appearance of a physical crack in the coating.

MEK Double Rubs: MEK double rub data was collected using a cotton swab wood stick saturated with methyl ethyl ketone (MEK). The saturated cotton swab is pushed forward and pulled back ~2" with one oscillation defined as a cycle. Failure is noted when a loss of gloss is noted.

X-Hatch Adhesion: Adhesion was tested using the procedure outlined in ASTM-3359 using 3M Scotch® Tape 898.

1" Conical Mandrel: Conical mandrel bend test data was collected using a BYK Gardner conical mandrel tester with failure noted at which diameter bend the coating cracks or peels.

Resin product 2 and 3 were coated onto cleaned cold rolled steel panels using a square draw down applicator with a 5 mil gap. Dry times were recorded in Table 1__ by touch and graded as 1=wet, 2=tacky, 3=dry-to-touch and 4=dried through. Films were allowed to cure in ambient conditions for 48 days and the coatings pendulum hardness in Table 2 was collected using a König pendulum.

TABLE 1

| | Dry Time | | | | | | | | | |
|---|---|---|---|---|---|---|---|---|---|---|
| Resin | ¼ hr | ½ hr | ¾ hr | 1 hr | 2 hr | 3 hr | 4 hr | 7 hr | 23 hr | 2 days |
| Product 2 (15% MeOH) | 1 | 1 | 1 | 1 | 1 | 1 | 1 | 1 | 4 | — |
| Product 3 (15% EtOH) | 1 | 1 | 1 | 1 | 1 | 1 | 1 | 1 | 3 | 4 |

TABLE 2

| Resin | König Pendulum Hardness (12°↔3°) | Dry Film Thickness (DFT) (mils) |
|---|---|---|
| Product 2 (15% MeOH) | 154 (48 days) | 2.0 |
| Product 3 (15% EtOH) | 249 (48 days) | 1.6 |

Resin products 2, 5, 10, 11, 12 and 13 were coated onto cleaned cold rolled steel panels using a square draw down applicator with a 10 mil gap. Films were allowed to cure in ambient conditions and the coating's pendulum hardness using a König pendulum was measured at 3, 7 and 14 days of cure time as shown in Table 3.

TABLE 3

| | | Pendulum Hardness (12°↔3°) | | |
|---|---|---|---|---|
| Resin | DFT (mils) | 3 day | 7 day | 14 day |
| Product 2 (15% MeOH) | 3.6 | 70 | 94 | 130 |
| Product 5 (10% BuAc) | | No Cure | | |
| Product 10 (15% MeOH) | 4.0 | 30 | 96 | 70 |
| Product 11 (10% MeOH) | 3.3 | 18 | 24 | 213 |
| Product 12 (10% MeOH) | 3.7 | 32 | 24 | 68 |
| Product 13 (10% MeOH) | 4.0 | 7 | 18 | 70 |

Product 10 was formulated into a pigmented coating using titanium dioxide as the pigment and spray coated with a spray gun onto cleaned cold rolled steel panels as shown in Table 4. A coating was subjected to Ultraviolet B (UVB) radiation and the coating's change in color and gloss was recorded over several days as shown in Table 5. The viscosity of the formulation in Table 4 was measured over several weeks as shown in Table 6. The coating's pendulum hardness using a König pendulum was measured over several weeks as shown in Table 7.

TABLE 4

| Material | Amount (g) | wt (%) |
|---|---|---|
| DuPont R-960 | 25.87 | 25.9% |
| Product 10 (30% MeOH) | 74.20 | 74.1% |
| Total | 100.07 | |

TABLE 5

| Time | 0 day | 1 day | 7 day |
|---|---|---|---|
| Delta E - UVB | | 1.1 | 2.6 |
| Gloss (60°) - UVB | 76.6 | 65 | 50.8 |

TABLE 6

| Time | 3 day | 17 day | 36 day |
|---|---|---|---|
| Viscosity (rt, RV-DV3, #5) | 140.8 cp | 139.6 cp | 155.2 cp |

TABLE 7

| Time | DFT (mils) | 1 day | 3 day | 7 day | 17 day |
|---|---|---|---|---|---|
| König Pendulum Hardness (12°↔3°) | 6.8 | 81 | 99 | 120 | 176 |

Figure 2:
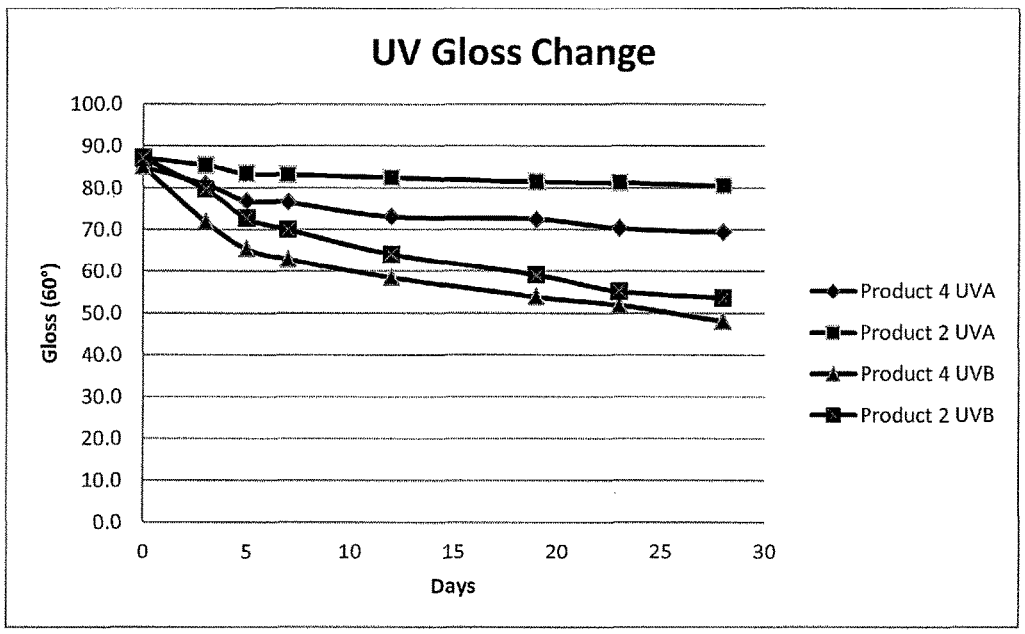
FIG. 2 is a chart illustrating the change of gloss 60 over time.

Product 2 and product 4 were formulated into pigmented coatings using titanium dioxide as the pigment as shown in Tables 8 and 10 respectively. The coatings were applied to cleaned cold rolled steel panels with a spray gun. Physical film properties were collected as shown in Tables 9 and 11 respectively. After 7 days of curing at ambient conditions the coatings were placed into a Q-Labs QUV chamber and subjected to constant UVB and UVA light. The delta E and 60° gloss were collected as a function of time as shown in FIGS. 1 and 2. Delta E is a standard measure of color change.

TABLE 8

| Material | Amount (g) | wt (%) |
|---|---|---|
| DuPont R-960 | 9.43 | 22.0% |
| Product 4 (10% EtOAc) | 26.15 | 61.0% |
| Butyl Acetate | 7.26 | 16.9% |
| Total | 42.84 | 100% |

TABLE 9
Product 4 Pigmented Coating Data

| | Day | | | | | |
|---|---|---|---|---|---|---|
| | 2 | 5 | 7 | 14 | 26 | 30 |
| König Pendulum Hardness (6°↔3°) | — | 14 | 16 | 14 | 15 | 15 |
| Pencil Hardness | — | — | <2B | 2B | — | B |
| Forward Impact Resistance (in-lbs) | — | — | — | 52 | — | 56 |
| MEK Double Rubs | — | — | — | — | — | >200 |
| X-Hatch Adhesion | — | — | — | — | — | 3B |
| 1" Conical Mandrel | — | — | — | — | — | Pass |

TABLE 10

| Material | Amount (g) | wt (%) |
|---|---|---|
| DuPont R-960 | 9.43 | 21.9% |
| Product 2 (10% EtOAc) | 26.20 | 60.7% |
| Butyl Acetate | 7.52 | 17.4% |
| Total | 43.15 | 100% |

TABLE 11
Product 2 Pigmented Coating Data

| | Day | | | | | |
|---|---|---|---|---|---|---|
| | 2 | 5 | 7 | 14 | 26 | 30 |
| König Pendulum Hardness (6°↔3°) | 10 | 47 | 55 | 94 | 94 | 88 |
| Pencil Hardness | — | — | H | H | — | 4H |
| Forward Impact Resistance (in-lbs) | — | — | — | 32 | — | 16 |
| MEK Double Rubs | — | — | — | — | — | >200 |
| X-Hatch Adhesion | — | — | — | — | — | 1B |
| 1" Conical Mandrel | — | — | — | — | — | Failed Peeled |

Figure 3:
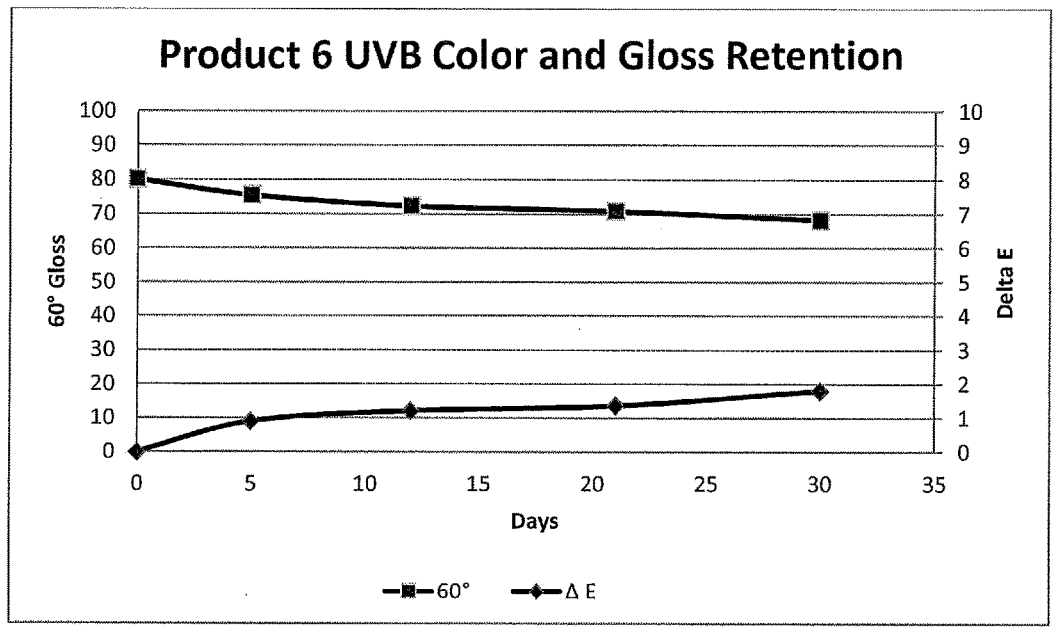
FIG. 3 is a chart illustrating Product 6's UVB Color and Gloss Retention over time.

Product 6 was formulated into a pigmented coating using titanium dioxide as the pigment as shown in Table 12. The coating was applied to cleaned cold rolled steel panels with a HVLP spray gun. Physical film properties of the pigmented were collected as shown in Table 13. After 7 days of curing at ambient conditions the coating was placed into a Q-Labs QUV chamber and subjected to constant UVB light. The delta E and 60° gloss were collected as a function of time as shown in FIG. 3.

TABLE 12

| Material | Amount (g) | wt (%) |
|---|---|---|
| DuPont R-960 | 9.54 | 19.1% |
| Product 6 (10% EtOAc) | 25.38 | 50.8% |
| Butyl Acetate | 15.07 | 30.1% |
| Total | 49.99 | 100% |

TABLE 13

| | Day | | | | |
|---|---|---|---|---|---|
| | 5 | 7 | 19 | 28 | 29 |
| König Pendulum Hardness (6°↔3°) | 19 | 60.5 | 95 | 95 | — |
| Pencil Hardness | — | 4H | 6H | 6H | — |
| Forward Impact Resistance (in-lbs) | — | — | — | 28 | — |
| MEK Double Rubs | — | — | — | — | >400 |
| X-Hatch Adhesion | — | — | — | <2B | — |
| 1" Conical Mandrel | — | — | — | Failed Peeled | — |

Figure 4:
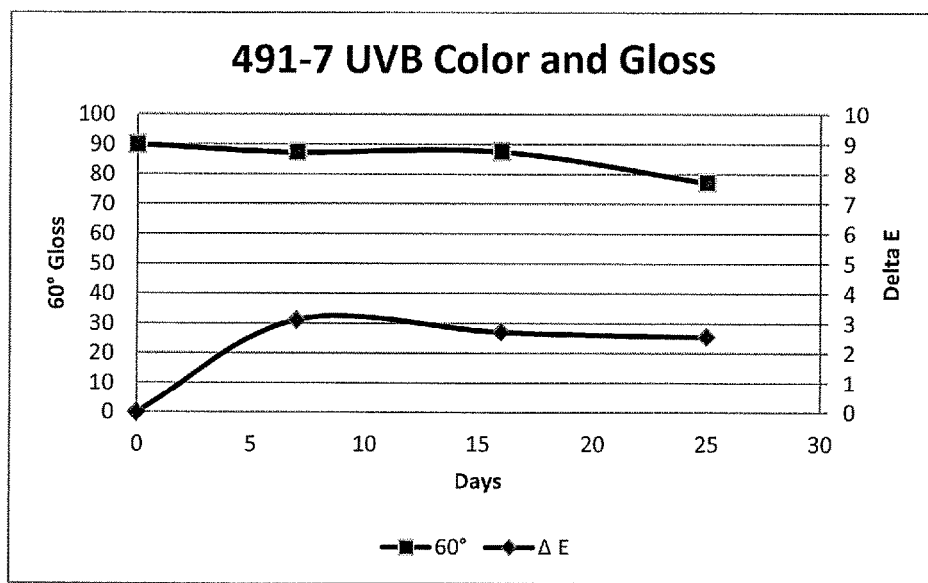
FIG. 4 is a chart illustrating 491-7 UVB Color and Gloss over time.

Product 7 was formulated into a pigmented coating using titanium dioxide as the pigment as shown in Table 14. The coating was applied to cleaned cold rolled steel panels with a HVLP spray gun. Physical film properties were collected as shown in Table 15. After 7 days of curing at ambient conditions the pigmented coating was placed into a Q-Labs QUV chamber and subjected to constant UVB light. The delta E and 60° gloss were collected as a function of time as shown in FIG. 4.

TABLE 14

| Material | Amount (g) | wt (%) |
|---|---|---|
| DuPont R-960 | 8.87 | 22.7% |
| Product 7 (15% Tol/EtOAc 1:1) | 26.12 | 66.8% |
| Butyl Acetate | 4.13 | 10.6% |
| Total | 39.12 | 100% |

TABLE 15

| | Day | | | |
|---|---|---|---|---|
| | 12 | 19 | 28 | 29 |
| König Pendulum Hardness (6°↔3°) | 6.5 | 14 | 13 | |
| Pencil Hardness | | <2B | <6B | |
| Forward Impact Resistance (in-lbs) | | — | 120 | |
| MEK Double Rubs | | — | — | <50 |
| X-Hatch Adhesion | | — | 3B | |
| 1" Conical Mandrel | | — | Pass | |

Figure 5:
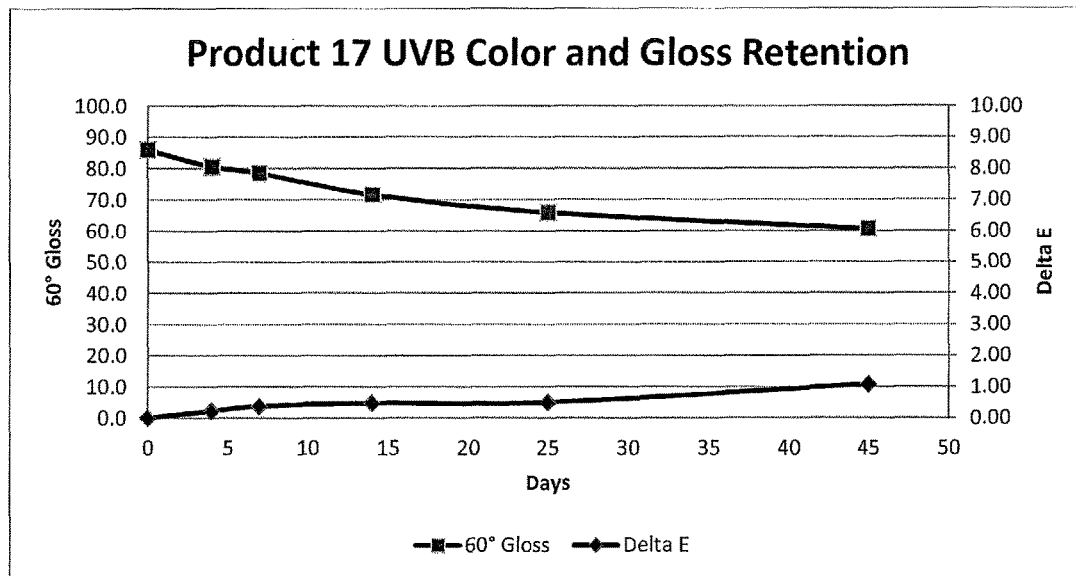
FIG. 5 is a chart illustrating Product 17's UVB Color and Gloss Retention over time.

Product 17 was formulated into a pigmented coating using titanium dioxide as the pigment as shown in Table 16. The coating was applied to cleaned cold rolled steel panels with a spray gun. A clear coat using product 17 was also applied to cold rolled steel panels using a spray gun as shown in Table 18. Physical film properties of the coatings were collected as shown in Tables 17 and 19 respectively. After 7 days of curing at ambient conditions the pigmented coating was placed into a Q-Labs QUV chamber and subjected to constant UVB light. The delta E and 60° gloss were collected as a function of time as shown in FIG. 5.

TABLE 16

| Material | Amount (g) | wt (%) |
|---|---|---|
| DuPont R-960 | 8.75 | 20.3% |
| Product 17 (30% MeOH/t-Butyl Acetate 1:1) | 31.26 | 72.7% |
| Butyl Acetate (aprox) | 3.00 | 7.0% |
| Total | 43.01 | 100% |

TABLE 17

Product 17 Pigmented Coating Data

| | Day | | | | | |
|---|---|---|---|---|---|---|
| | 1 | 4 | 7 | 14 | 21 | 32 |
| König Pendulum Hardness (12°↔3°) | 21 | 147.5 | 119 | 220 | 225 | 230.5 |
| Pencil Hardness | | | 5H | 6H | | 6H |
| Forward Impact Resistance (in-lbs) | | | | 28 | | 24 |
| X-Hatch Adhesion | | | | | | <2B |
| 1" Conical Mandrel | | | | fail | | Peeled |

TABLE 18

| Material | Amount (g) | wt (%) |
|---|---|---|
| DuPont R-960 | 0 | 0.0% |
| Product 17 (30% MeOH/t-Butyl Acetate 1:1) | 14.61 | 90.5% |
| Butyl Acetate (aprox) | 1.53 | 9.5% |
| Total | 16.14 | 100% |

TABLE 19

Product 17 Clear Coat Data

| | Day | | | | |
|---|---|---|---|---|---|
| | 1 | 4 | 7 | 14 | 32 |
| Pencil Hardness | | | | 4H | 4H |
| Forward Impact Resistance (in-lbs) | | | | 32 | 32 |
| X-Hatch Adhesion | | | | | 4B |
| 1" Conical Mandrel | | | | Fail | Cracked |

Product 8 was formulated into a pigmented coating using titanium dioxide as the pigment as shown in Table 20. The coating was applied to cleaned cold rolled steel panels with a spray gun. A clear coat using product 8 was also applied to cold rolled steel panels using a spray gun as shown in Table 23. Physical film properties of the coatings were collected as shown in Tables 21, 22, and 24. After 7 days of curing at ambient conditions the pigmented coating was placed into a Q-Labs QUV chamber and subjected to constant UVB light. The delta E and 60° gloss were collected as a function of time as shown in Table 22.

TABLE 20

| Material | Amount (g) | wt (%) |
|---|---|---|
| DuPont R-960 | 7.98 | 23.4% |
| Product 8 (10% Toluene) | 22.05 | 64.6% |
| Butyl Acetate | 3.07 | 9.0% |
| DPMAc | 1.02 | 3.0% |
| Total | 34.12 | 100% |

TABLE 21

Product 8 Pigmented Coating Data

| | Day | |
|---|---|---|
| | 3 | 10 |
| König Pendulum Hardness (6°↔3°) | 7 | 84 |

TABLE 22

Product 8 Pigmented Coating Data

| | Day | |
|---|---|---|
| | 0 | 17 |
| Delta E | 0 | 20.7 |
| Gloss 60° | 88.7 | 24.4 |

TABLE 23

| Material | Amount (g) | wt (%) |
|---|---|---|
| DuPont R-960 | 0 | 0.0% |
| Product 8 (10% Toluene) | 15.06 | 88.2% |
| Butyl Acetate | 1.51 | 8.8% |
| DPMAc | 0.50 | 3.0% |
| Total | 17.07 | 100% |

TABLE 24

Product 8 Clear Coat Data

| | Day | |
|---|---|---|
| | 3 | 10 |
| König Pendulum Hardness (6°↔3°) | 6 | 113 |

Figure 6:
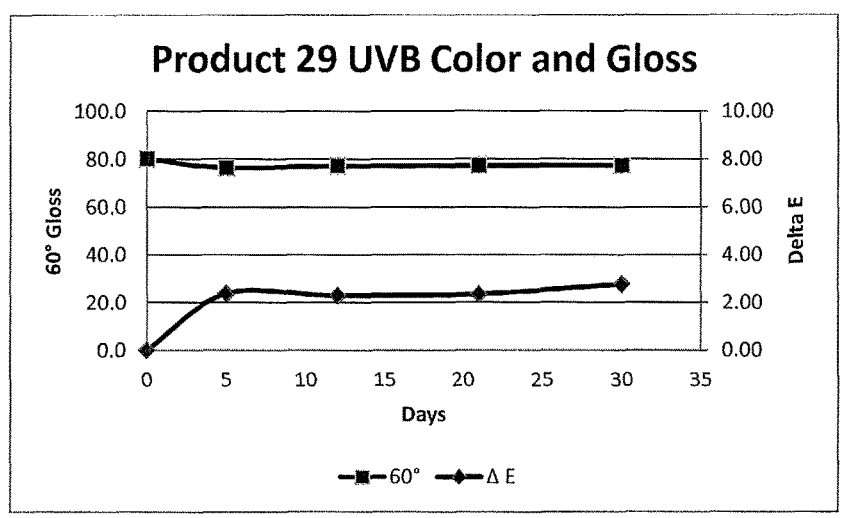
FIG. 6 is a chart illustrating Product 29's UVB Color and Gloss over time.

Product 29 was formulated into a pigmented coating using titanium dioxide as the pigment as shown in Table 25. The coating was applied to cleaned cold rolled steel panels with a spray gun. Physical film properties of the coatings were collected as shown in Table 26. After 7 days of curing at ambient conditions the pigmented coating was placed into a Q-Labs QUV chamber and subjected to constant UVB light. The delta E and 60° gloss were collected as a function of time as shown in FIG. 6.

TABLE 25

| Material | Amount (g) | wt (%) |
|---|---|---|
| DuPont R-960 | 7.037 | 17.0% |
| Product 29 (37% Toluene) | 28.07 | 68.0% |
| Butyl Acetate | 6.17 | 14.9% |
| Total | 41.28 | 100% |

TABLE 26

| | Day | | | | |
|---|---|---|---|---|---|
| | 5 | 7 | 19 | 28 | 29 |
| König Pendulum Hardness (6°↔3°) | 11 | 22 | 23 | 27 | — |
| Pencil Hardness | — | <2B | B | H | — |
| Forward Impact Resistance (in-lbs) | — | — | — | 16 | — |
| MEK Double Rubs | — | — | — | — | <50 |
| X-Hatch Adhesion | — | — | — | <2B | — |
| 1" Conical Mandrel | — | — | — | Pass | — |

Figure 7:
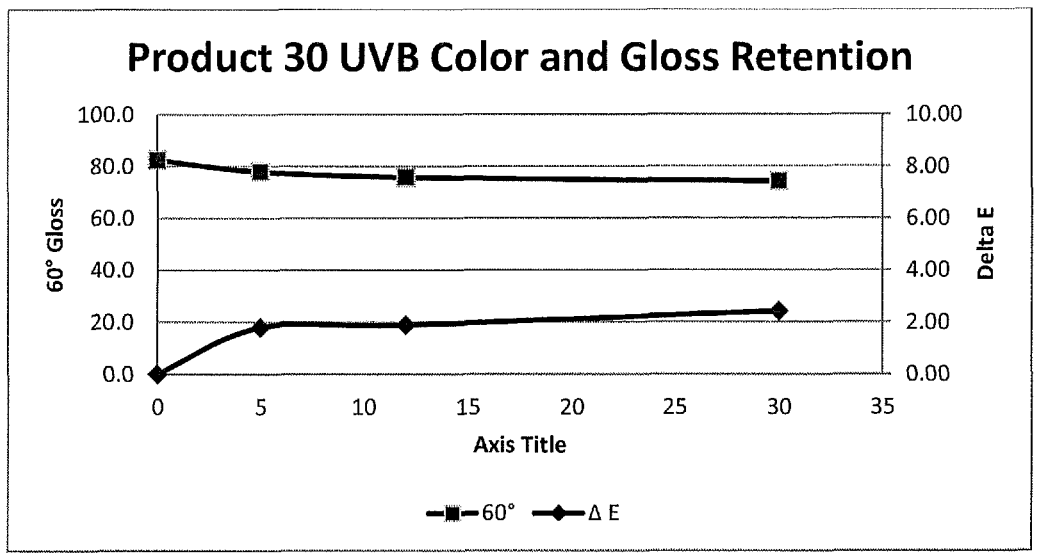
FIG. 7 is a chart illustrating Products 30's UVB Color and Gloss Retention over time.

Product 30 was formulated into a pigmented coating using titanium dioxide as the pigment as shown in Table 27. The coating was applied to cleaned cold rolled steel panels with a HVLP spray gun. Physical film properties of the coatings were collected as shown in Table 28. After 7 days of curing at ambient conditions the pigmented coating was placed into a Q-Labs QUV chamber and subjected to constant UVB light. The delta E and 60° gloss were collected as a function of time as shown in FIG. 7.

TABLE 27

| Material | Amount (g) | wt (%) |
|---|---|---|
| DuPont R-960 | 7.388 | 17.8% |
| Product 30 (33% Toluene) | 27.66 | 66.5% |
| Butyl Acetate | 6.55 | 15.7% |
| Total | 41.60 | 100% |

TABLE 28

| | Day | | | | |
|---|---|---|---|---|---|
| | 5 | 7 | 19 | 28 | 29 |
| König Pendulum Hardness (6°↔3°) | 9 | 20 | 22 | 27 | — |
| Pencil Hardness | — | <2B | HB | 3H | — |
| Forward Impact Resistance (in-lbs) | — | — | — | 12 | — |
| MEK Double Rubs | — | — | — | — | <50 |
| X-Hatch Adhesion | — | — | — | 4B | — |
| 1" Conical Mandrel | — | — | — | Pass | — |

While the present invention has been described and illustrated by reference to particular embodiments, those of ordinary skill in the art will appreciate that the invention lends itself to variations not necessarily illustrated herein. For example, the alkali metal containing compound may be added as such or generated in-situ in the compositions of the invention. For this reason, then, reference should be made solely to the appended claims for purposes of determining the true scope of the present invention.

What is claimed is:
1. A composition comprising
(a) a silane functionalized compound having the formula 1:

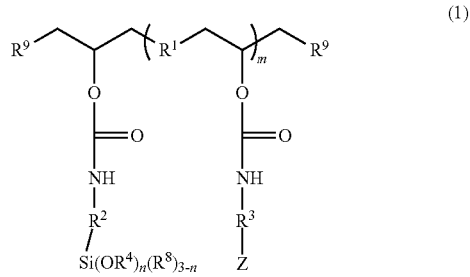

(1)

wherein
each $R^1$ is independently selected from the group consisting of a saturated or unsaturated, linear, branched or cyclic aliphatic group having up to 30 carbon atoms, a heterocyclic group having from 3 to 30 carbon atoms, and an aromatic group having from 6 to 30 carbon atoms, where $R^1$ has the formula:

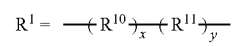

wherein $R^{10}$ is a cyclic aliphatic group or heterocyclic group of from 3 to 30 carbon atoms or an aromatic group and $R^{11}$ is an aliphatic group selected from the group consisting of linear or branched alkylene of from 1 to 30 carbon atoms, x is from 0 to 20, y is from 0 to 20, and wherein $R^1$ has at least a non-zero x or a non-zero y;

each $R^2$ and $R^3$ independently is an alkylene group having from 1 to 30 carbon atoms, a cycloalkylene group having from 3 to 30 carbon atoms, or an arylene group having from 6 to 30 carbon atoms;

$R^4$ is an alkyl group with 1 to 8 carbon atoms;

$R^8$ is an alkyl group with 1 to 10 carbon atoms;

$R^9$ is morpholino or an amino-functional group $R^{12}$, having the general formula:

$$N(R^5D)_a(R^6D)_b,$$

wherein $R^5$ and $R^6$ is independently phenylene or $(-CHR^{13}-)_f$, where f is from 1 to 20, and $R^{13}$ is hydrogen or a hydrocarbon group from 1 to 10 carbon atoms, D is a hydrogen atom, an alkoxysilane moiety or a —O(CO)NH—$R^3$—Z group, a is from 0 to 2 and b is from 0 to 2, where one of a or b is a non-zero number and a+b=2, and Z is a hydrogen atom or $Si(OR^4)_n(R^8)_{3-n}$ group where n is 1 to 3;

each Z independently is a hydrogen atom or $Si(OR^4)_n (R^8)_{3-n}$ group;

m is greater than or equal to 1;

n is from 1 to 3, and where the silane functionalized compound is free of hydroxyl and epoxy group, and (b) a catalyst, and (c) a polymeric resin.

2. The composition of claim 1, wherein the silane functionalized compound having the formula 1 comprises, as a weight percentage of the composition, an amount from about 5 weight percent to about 80 weight percent.

3. The composition of claim 1, wherein the catalyst is a metal organic compound.

4. The composition of claim 1, wherein when the catalyst is present, the catalyst comprises from about 0.01 weight percent to about 10 weight percent of the composition.

5. The composition of claim 1 wherein the polymeric resin is selected from the group consisting of amine resins, epoxy resins, polydimethylsiloxane resins, acrylic resins, other organo-functionalized polysiloxane resins, polyimide resins, fluorocarbon resins, benzocyclobutene resins, fluorinated polyallyl ethers, polyamide resins, polyimidoamide resins, phenol cresol resins, aromatic polyester resins, polyphenylene ether (PPE) resins, bismaleimide resins, fluororesins, and combinations thereof.

6. The composition of claim 5, wherein the composition further comprises an amine-containing curing agent, an amide-containing curing agent, or both, with each curing agent having one or more active hydrogen atoms.

7. The composition of claim 6, wherein the curing agent comprises from about 0.1 weight percent to about 2 weight percent of the composition.

8. The composition of claim 1, wherein the composition further comprises a solvent.

9. The composition of claim 1, wherein the composition further comprises inorganic fillers, additional flame retardants, dyes, pigments, surfactants, flow control agents, and combinations thereof.

10. The composition of claim 1, wherein m is 1.

11. The composition of claim 1, wherein the silane functionalized compound has a weight average molecular weight of from about 350 to about 500,000.

12. The composition of claim 1, wherein $R^1$ is

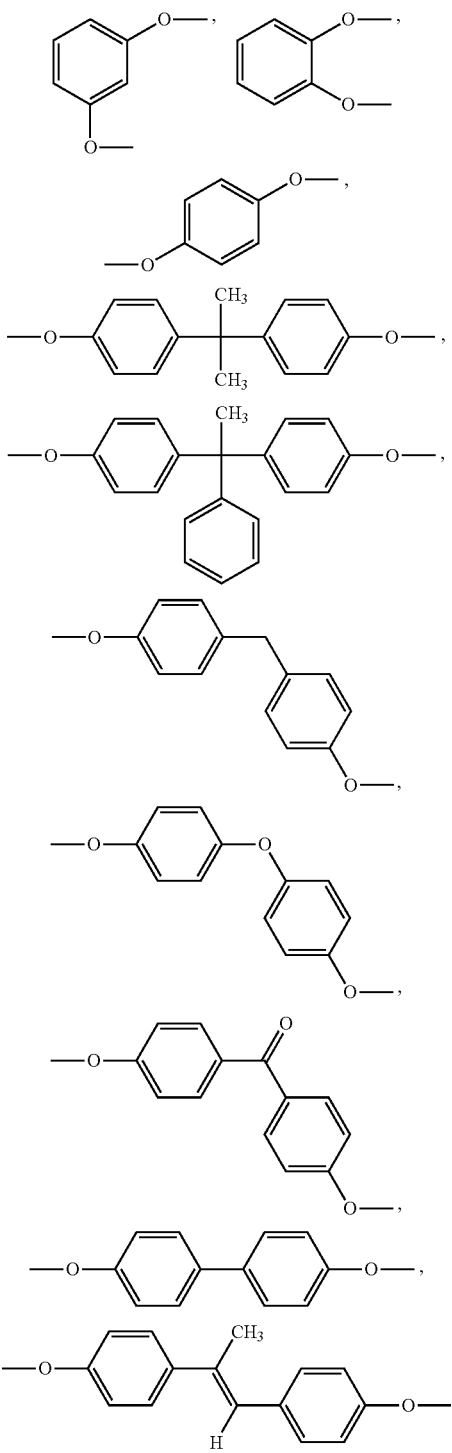

or combinations thereof.

13. The composition of claim 1, wherein $R^9$ is an amino-functional group selected from the group consisting of diethylamino, morpholino, bis(tri-methoxysilylpropyl)amino, and N-ethyl-N-trimethoxysilylisobutylamino.

14. The composition of claim 1, wherein the silane functionalized compound having the formula 1 is

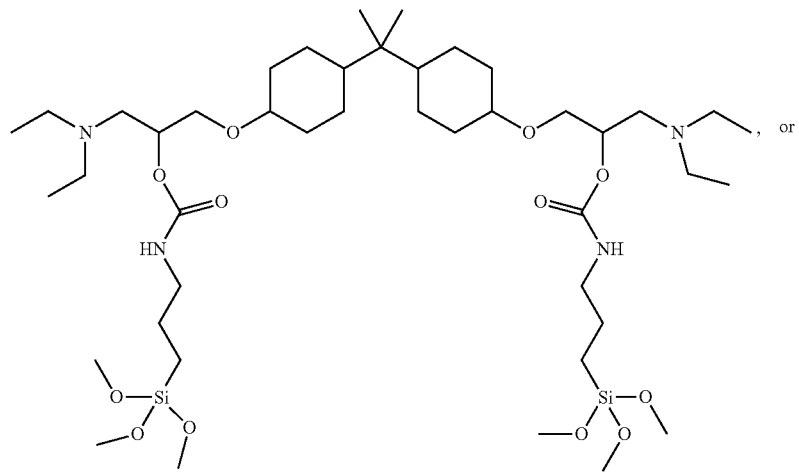

, or

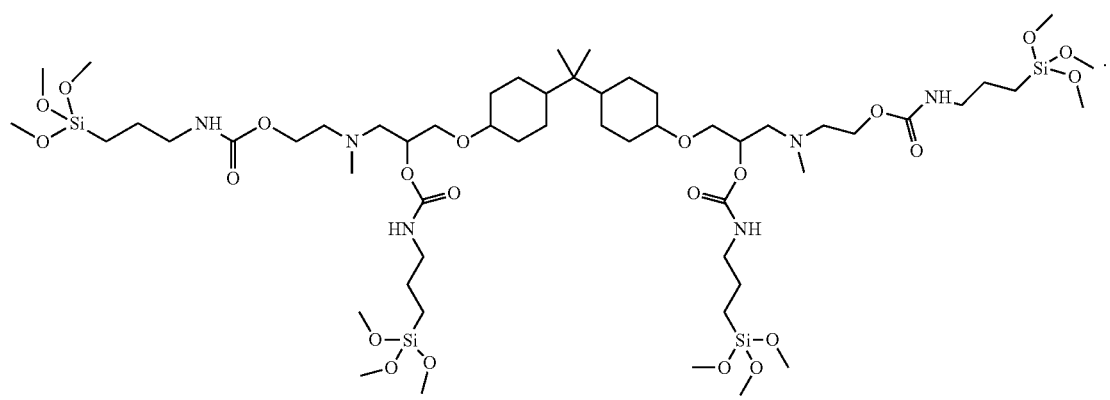

15. The composition of claim 1, wherein the silane functionalized compound having the formula 1 is formed from a process comprising:
(a) opening glycidyl units of an epoxy resin with a secondary amine to form hydroxyl groups; and
(b) reacting the hydroxyl groups formed in step (a) with an (alkoxysilyl)alkyl isocyanate or a mixture of an alkoxysilane)alkyl isocyanate and a non-silyl containing isocyanate to form the silane functionalized compound having the formula 1.

16. The composition of claim 15, wherein the epoxy resin of step (a) is chain extended with a suitable bifunctional reactant to provide a chain extended epoxy resin comprising secondary hydroxyl groups pendant to the epoxy resin derived backbone.

17. The composition of claim 1, wherein the silane functionalized compound having formula (1) contains at least one Z group which is a hydrogen atom.

18. The composition of claim 1, wherein $R^1$ further comprises at least one heteroatom, wherein $R^{11}$ further comprises at least one heteroatom, or a combination thereof.

19. A silane functionalized compound having the formula 1:

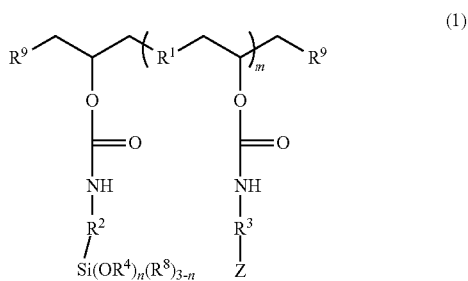

(1)

wherein
each $R^1$ is independently selected from the group consisting of a saturated or unsaturated, linear, branched or cyclic aliphatic group having up to 30 carbon atoms, a heterocyclic group having from 3 to 30 carbon atoms, and an aromatic group having from 6 to 30 carbon atoms, where $R^1$ has the formula:

$$R^1 = -(R^{10})_x(R^{11})_y-$$

wherein $R^{10}$ is a cyclic aliphatic group or heterocyclic group of from 3 to 30 carbon atoms or an aromatic group and $R^{11}$ is an aliphatic group selected from the group consisting of linear or branched alkylene of from 1 to 30 carbon atoms, x is from 0 to 20, y is from 0 to 20, and wherein $R^1$ has at least a non-zero x or a non-zero y or both a non-zero x and a non-zero y;

each $R^2$ and $R^3$ independently is an alkylene group having from 1 to 30 carbon atoms, a cycloalkylene group having from 3 to 30 carbon atoms, or an arylene group having from 6 to 30 carbon atoms;

$R^4$ is an alkyl group with 1 to 8 carbon atoms;
$R^8$ is an alkyl group with 1 to 10 carbon atoms;
$R^9$ is an amino-functional group, $R^{12}$, having the general formula:

$$N(R^5D)_a(R^6D)_b,$$

wherein $R^5$ and $R^6$ is independently be phenylene or $(-CHR^{13}-)_f$, where f is from 1 to 20, and $R^{13}$ is hydrogen or a hydrocarbon group from 1 to 10 carbon atoms, D is a hydrogen atom or $-O(CO)NH-R^3-Z$ group, a is from 0 to 2 and b is from 0 to 2, where one of a or b is a non-zero number and a+b=2, and Z is a hydrogen atom or $Si(OR^4)_n(R^8)_{3-n}$ group where n is 1 to 3;

each Z independently is a hydrogen atom or $Si(OR^4)_n(R^8)_{3-n}$ group;

m is greater than or equal to 1;

n is from 1 to 3, and where the silane functionalized compound is free of hydroxyl and epoxy groups, wherein $R^1$ optionally has at least one heteroatom, and wherein $R^{11}$ optionally has at least one heteroatom.

20. The composition of claim 19, wherein the silane functionalized compound having formula (1) contains at least one Z group which is a hydrogen atom.

* * * * *